(12) United States Patent
Fisk et al.

(10) Patent No.: US 7,033,831 B2
(45) Date of Patent: Apr. 25, 2006

(54) ISLET CELLS FROM HUMAN EMBRYONIC STEM CELLS

(75) Inventors: Gregory J. Fisk, Fremont, CA (US); Margaret S. Inokuma, San Jose, CA (US)

(73) Assignee: Geron Corporation, Menlo Park, CA (US)

( * ) Notice: Subject to any disclaimer, the term of this patent is extended or adjusted under 35 U.S.C. 154(b) by 329 days.

(21) Appl. No.: 10/313,739

(22) Filed: Dec. 6, 2002

(65) Prior Publication Data

US 2003/0138948 A1    Jul. 24, 2003

Related U.S. Application Data

(60) Provisional application No. 60/338,885, filed on Dec. 7, 2001.

(51) Int. Cl.
*C12N 5/02* (2006.01)
(52) U.S. Cl. .................................. 435/377; 435/366
(58) Field of Classification Search ................ 435/363, 435/366, 377, 69.4, 375
See application file for complete search history.

(56) References Cited

U.S. PATENT DOCUMENTS

| | | | |
|---|---|---|---|
| 4,378,016 A | 3/1983 | Loeb | 128/260 |
| 4,391,909 A | 7/1983 | Lim | 435/178 |
| 4,439,521 A | 3/1984 | Archer et al. | 435/1 |
| 4,797,213 A | 1/1989 | Parisius et al. | 210/651 |
| 5,674,289 A | 10/1997 | Fournier et al. | 623/11 |
| 5,834,308 A | 11/1998 | Peck et al. | 435/325 |
| 5,888,705 A | 3/1999 | Rubin et al. | 435/366 |
| 5,888,816 A | 3/1999 | Coon et al. | 435/366 |
| 5,902,577 A | 5/1999 | Asfari et al. | 424/93.21 |
| 5,919,703 A | 7/1999 | Mullen et al. | 435/381 |
| 5,928,942 A | 7/1999 | Brothers | 435/347 |
| 6,023,009 A | 2/2000 | Stegemann et al. | 623/11 |
| 6,090,622 A | 7/2000 | Gearhart et al. | 435/366 |
| 6,197,945 B1 | 3/2001 | Edlund | 536/23.1 |
| 6,200,806 B1 | 3/2001 | Thomson | 435/366 |
| 6,326,201 B1 | 12/2001 | Fung et al. | 435/377 |
| 6,436,704 B1 | 8/2002 | Roberts et al. | 435/366 |
| 6,610,535 B1 | 8/2003 | Lu et al. | 435/325 |

FOREIGN PATENT DOCUMENTS

| | | |
|---|---|---|
| WO | WO 99/20741 | 4/1999 |
| WO | WO 00/47720 | 8/2000 |
| WO | WO 00/47721 | 8/2000 |
| WO | WO 00/72885 | 12/2000 |
| WO | WO 00/78929 | 12/2000 |
| WO | WO 01/11011 | 2/2001 |
| WO | WO 01/39784 | 6/2001 |
| WO | WO 01/51610 | 7/2001 |
| WO | WO 01/51616 | 7/2001 |
| WO | WO 01/77300 | 10/2001 |
| WO | WO 01/81549 | 11/2001 |
| WO | WO 02/059278 | 8/2002 |
| WO | WO 02/074946 | 9/2002 |
| WO | WO 02/074948 | 9/2002 |
| WO | WO 02/079457 | 10/2002 |
| WO | WO 02/086107 | 10/2002 |
| WO | WO 02/092756 | 11/2002 |
| WO | WO 02/096203 | 12/2002 |
| WO | WO 03/029445 | 4/2003 |

OTHER PUBLICATIONS

Portela-Gomes et al. IGF-II in Human Fetal and Adult Pancreas. Journal of Endocrinology. 2000, vol. 165, pp. 245-251.*
Thomson et al. Isolation of a Primate Embryonic Stem Cell Line. Proceedings of the National Academy of Sciences (USA). 1995, vol. 92:7844-7848.*
Lim et al. Proteome Analysis of Conditioned Medium from Mouse Embryonic Fibroblast Feeder Layers which Support the Growth of Human Embryonic Stem Cells. Proteomics. 2002, vol. 2, pp. 1187-1203.*
Demeterco et al. A Role for Activin A and Betacellulin in Human Fetal Pancreatic Cell Differentiation and Growth. J. Clinical Endocrin. & Metabol. 2000, vol. 85, 3892-3897.*
Bonner-Weir et al. In Vitro Cultivation of Human Islets from Expanded Ductal Tissue. Proced. National Acad. Sci. 2000, vol. 97, pp. 7999-8004.*
Schuldiner et al. Effects of Eight Growth Factors on the Differentiation of Cells derived from Human Embryonic Stem Cells. Proceedings of the National Academy of Sciences (USA). 2000, 97, pp. 11307-11312.*

(Continued)

*Primary Examiner*—Deborah Crouch
(74) *Attorney, Agent, or Firm*—J. Michael Schiff; Bart W. Wise; David J. Earp

(57) ABSTRACT

This disclosure provides a system for producing pancreatic islet cells from embryonic stem cells. Differentiation is initiated towards endoderm cells, and focused using reagents that promote emergence of islet precursors and mature insulin-secreting cells. High quality populations of islet cells can be produced in commercial quantities for use in research, drug screening, or regenerative medicine.

10 Claims, 7 Drawing Sheets

OTHER PUBLICATIONS

Figure 1:
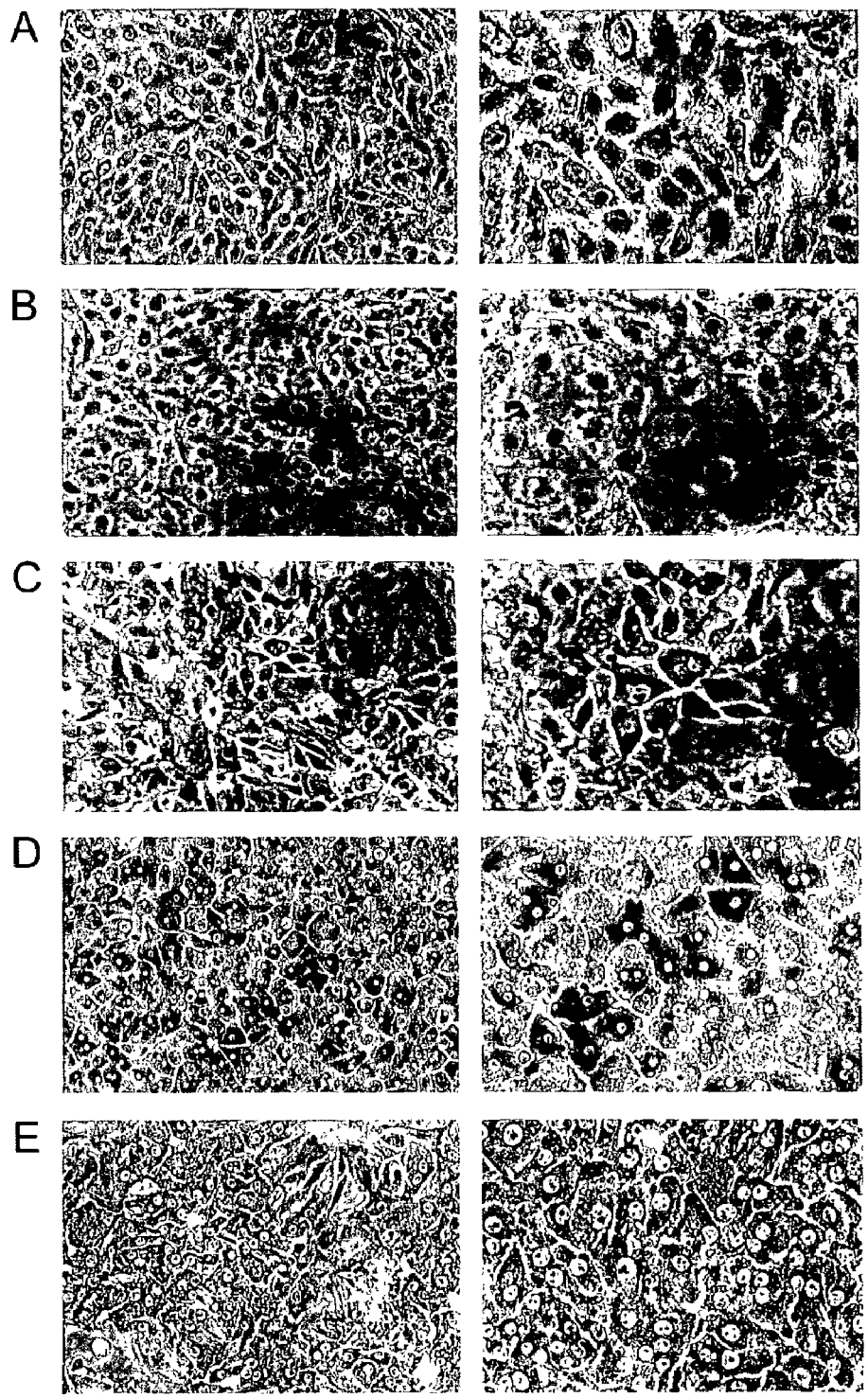

Mashima et al. Betacellulin and Activin A Coordinately Convert Amylase-Secreting Pancreatic AR42J Cells into Insulin-Secreting Cells. J. Clinical Investigation. 1996, vol. 97, pp. 1647-1654.*

Abraham EJ et al, Insulinotropic Hormone Glucagon-Like Peptide-1 Differentiation of Human Pancreatic Islet-Derived Progenitor Cells into Insulin-Producing Cells, Endocrinology 143(8):3152 (Aug. 2002).

Amit M et al, Derivation and Spontaneous Differentiation of Human Embryonic Stem Cells, J Anat 200:225 (2002).

Apelqvist A et al, Notch Signalling Controls Pancreatic Cell Differentiation, Nature 400(6747):877 (Aug. 1999).

Assady S et al, Insulin Production by Human Embryonic Stem Cells, Diabetes 50(8):1691 (Aug. 2001).

Beattie GM et al, Regulation of Proliferation and Differentiation of Human Fetal Pancreatic Islet Cells by Extracellular Matrix, Hepatocyte Growth Factor, and Cell-Cell Contact, Diabetes 45:1223 (Sep. 1996).

Blyszczuk P et al, Expression of Pax4 In Embryonic Stem Cells Promotes Differentiation of Nestin-Positive Progenitor and Insulin-Producing Cells, PNAS 100(3):998 (Feb. 2003).

Bretzel RG et al, Islet Transplantation: Present Clinical Situation and Future Aspects, Exp Clin Endocrinol Diabetes 109 (Suppl 2):S384 (2001).

Deutsch G et al, A Bipotential Precursor Population for Pancreas and Liver Within the Embryonic Endoderm, Dev 128:871 (2001).

Gradwohl G et al, Neurogenin3 is Required for the Development of the Four Endocrine Cell Lineages of the Pancreas, PNAS 97(4):1607 (Feb. 2000).

Hayek A et al, Experimental Transplantation of Human Fetal and Adult Pancreatic Islets, J Clin Endocri Metab 82(8): 2471 (1997).

Hori Y et al, Growth Inhibitors Promote Differentiation of Insulin-Producing Tissue from Embryonic Stem Cells, PNAS 99(25):16105 (Dec. 2002).

Jacobson L et al, Differentiation of Endoderm Derivatives, Pancreas and Intestine, from Rhesus Embryonic Stem Cells, Transpl Proc 33:674 (2001).

Kaczorowski DJ et al, Glucose-Resposive Insulin-Producing Cells from Stem Cells, Diabetes Metab Res Rev 18(6): 442 (Nov./Dec. 2002).

Keymeulen B et al, Implantation of Standarized Beta-Cell Grafts in a Liver Segment of IDDM Patients: Graft and Recipient Characteristics in Two Cases of Insulin-Independence Under Maintenance Immunosuppression for Prior Kidney Graft, Diabetologia 41:452 (1998).

Kim SK et al, Intercellular Signals Regulating Pancreas Development and Function, Genes Dev 15:111 (2001).

Lumelsky N et al, Differentiation of Embryonic Stem Cells to Insulin-Secreting Structure Similar to Pancreatic Islets, Science 292(5520):1389 (May 2001).

Oberholzer J et al, Clinical Islet Transplantation: A Review, Ann NY Acad Sci 875:189 (1999).

Odorico J et al, Pancreatic Gene Expression in Differentiating Embryonic Stem Cells, Keystone Symposium (Jan. 2000) Abstract.

Peck AB et al, Pancreatic Stem Cells: Building Blocks for a Better Surrogate Islet to Treat Type 1 Diabetes, Ann Med 33(3):186 (Apr. 2001).

Roep BO et al, Auto- and Alloimmune Reactivity to Human Islet Allografts Transplanted into Type 1 Diabetic Patients, Diabetes 48:484 (Mar. 1999).

Shamblott MJ et al, Derivation of Pluripotent Stem Cells from Cultured Human Primordial Germ Cells, PNAS 95: 13726 (Nov. 1998).

Soria B et al, Insulin-Secreting Cells Derived from Embrynic Stem Cells Normalize Glycemia in Streptozotocin-Induced Diabetic Mice, Diabetes 49(2):157 (Feb. 2000).

Soria B, In-Vitro Differentiation of Pancreatic Beta-Cells, Differentiation 68(4-5):205 (Oct. 2001).

Thomson JA et al, Embryonic Stem Cell Lines Derived from Human Blastocysts, Science 282:114 (Nov. 1998).

Yamaoka T et al, Development of Pancreatic Islets (Review), Int J Mol Med 3:247 (1999).

Yang L et al, In Vitro Trans-Differentiation of Adult Hepatic Stem Cells Into Pancreatic Endocrine Hormone-Producing Cells, PNAS 99(12):8078 (Jun. 2002).

Yoshida K et al, Genetic and Immunological Basis of Autoimmune Diabetes in the NOD Mouse, Rev Immuogenetics 2:140 (2000).

Zulewski H et al, Multipotetial Nestin-Positive Stem Cells Isolated from Adult Pancreatic Islets Differentiate ex Vivo into Pancreatic Endocrine, Exocrine, and Hepatic Phenotypes, Diabetes 50:521 (Mar. 2001).

Soria B et al, From Stem Cells to Beta Cells: New Strategies in Cell Therapy of Diabetes Mellitus, Diabetologia 44:407 (2001).

Wang H et al, Pdx1 Level Defines Pancreatic Gene Expression Pattern and Cell Lineage Differentiation, J Biol Chem 276(27):25279 (2001).

* cited by examiner

Insulin Expression by hESC-derived Islet Cells

DAPI

Insulin staining

A

B

C

Glucagon Expression by Cells Transfected with Neurogenin3

20x

40x

ISLET CELLS FROM HUMAN EMBRYONIC STEM CELLS

REFERENCE TO RELATED APPLICATION

This application claims priority to U.S. provisional application No. 60/338,885, filed Dec. 7, 2001. The priority application is hereby incorporated herein by reference in its entirety.

TECHNICAL FIELD

This invention relates generally to the fields of cell biology, embryonic stem cells, and cell differentiation. More specifically, this invention provides differentiated cells with pancreatic endocrine function.

BACKGROUND

The American Diabetes Association estimates that there are currently 5 million people in the United States with confirmed diabetes, and over 10 million at risk.

The cost of this disease and its sequelae to the American economy is staggering. Care of diabetics consumes a total of $98 billion per year, accounting for one of every seven healthcare dollars spent in the U.S. There are 24,000 new cases of diabetes-caused blindness caused by diabetes each year. Diabetes is the leading cause of kidney failure, contributing about 40% of new dialysis patients. Diabetes is also the most frequent cause of lower limb amputation, with 56,000 limbs lost to diabetes each year. The per capita health care costs incurred per diabetic person is $10,071 annually, compared with $2,669 for non-diabetics.

Type I diabetes mellitus (also known as insulin-dependent diabetes) is a severe condition accounting for 5-10% all diabetics. The pathology arises because the patient's insulin-secreting beta cells in the pancreas have been eliminated by an autoimmune reaction. Under current practice, the condition is managed by regular injection of insulin, constant attention to diet, and continuous monitoring of blood glucose levels to adjust the insulin dosing. It is estimated that the market for recombinant insulin will reach $4 billion by 2005. Of course, the availability of insulin is life-saving for Type I diabetics. But there is no question that the daily regimen of administration and monitoring that diabetics must adhere to is toublesome to the end user, and not universally effective.

For this reason, there are several clinical tests underway to transplant diabetics with islet cells isolated from donor pancreas. This has been made possible by recent advances in the isolation and culture of islet cells. U.S. Pat. No. 4,797, 213 described separation of islets of Langerhans. U.S. Pat. No. 4,439,521 reports a method for producing self-reproducing pancreatic islet-like structures. U.S. Pat. No. 5,919, 703 reports preparation and storage of pancreatic islets. U.S. Pat. No. 5,888,816 reports cell culture techniques for pancreatic cells using hypothalamus and pituitary extracts. WO 00/72885 reports methods of inducing regulated pancreatic hormone production in non-pancreatic islet tissues. WO 00/78929 reports methods of making pancreatic islet cells. Kim et al. (Genes Dev. 15:111, 2001) review the intercellular signals regulating pancreas development and function. Yamaoka et al. (Int. J. Mol. Med. 3:247, 1999) review the development of pancreatic islets, and the putative role of factors such as Sonic hedgehog and activin, transcriptional factors like PDX1 and Isl1, growth factors like EGF and HGF, hormones like insulin and growth hormone, and cell adhesion molecules such as N-CAM and cadherins.

Peck et al. (Ann. Med. 33:186, 2001) propose that pancreatic stem cells be used as building blocks for better surrogate islets for treating Type I diabetes. WO 00/47721 reports methods of inducing insulin positive progenitor cells. WO 01/39784 reports pancreatic stem cells isolated from islet cells that are nestin-positive. WO 01/77300 reports human pancreatic epithelial progenitors that are proposed to have the capacity to differentiate into acinar, ductal, and islet cells. Deutsch et al. (Development 128:871, 2001) describe a bipotential precursor population for pancreas and liver within the embryonic endoderm. Zulewski et al. (Diabetes 50:521, 2001) describe multipotential nestin-positive stem cells isolated from adult pancreatic islets that differentiate into endocrine, exocrine, and hepatic phenotypes. U.S. Pat. No. 6,326,201 (Curis Inc.) reports pancreatic progenitor cells made by dissociating and culturing cells from pancreatic duct. The present clinical experience of islet cell transplantation is reviewed by Bretzel et al. (Exp. Clin. Endocrinol. Diabetes 190 (Suppl. 2):S384, 2001) and Oberholzer et al. (Ann. N.Y. Acad. Sci. 875:189, 1999). The current clinical trials typically involve infusing cells from at least two pancreas donors. Even if this treatment proves to be successful, there will be insufficient material available from current sources to treat all the eligible Type I diabetic patients.

Developmental work has been done in several institutions to capitalize on the promise of pluripotent stem cells from the embryo to differentiate into other cell types. Cells bearing features of the islet cell lineage have reportedly been derived from embryonic cells of the mouse. For example, Lumelsky et al. (Science 292:1389, 2001) report differentiation of mouse embryonic stem cells to insulin-secreting structures similar to pancreatic islets. Soria et al. (Diabetes 49:157, 2000) report that insulin-secreting cells derived from mouse embryonic stem cells normalize glycemia in streptozotocin-induced diabetic mice.

Regrettably, the mouse model of embryonic stem cell development is its own peculiar case, and does not yield strategies for differentiation that are applicable to other species. In fact, pluripotent stem cells have been reproducibly isolated from very few other mammalian species. Only recently did Thomson et al. isolate embryonic stem cells from human blastocysts (Science 282:114, 1998). Concurrently, Gearhart and coworkers derived human embryonic germ (hEG) cell lines from fetal gonadal tissue (Shambloft et al., Proc. Natl. Acad. Sci. USA 95:13726, 1998). Unlike mouse embryonic stem cells, which can be kept from differentiation simply by culturing with Leukemia Inhibitory Factor (LIF), human embryonic stem cells must be maintained under very special conditions (U.S. Pat. No. 6,200, 806; WO 99/20741; WO 01/51616). Accordingly, it is necessary to develop completely new paradigms to differentiate human pluripotent cells into fully functional differentiated cell types.

Jacobson et al. (Transplant. Proc. 33:674, 2001) reported differentiation of intestinal and pancreatic endoderm from rhesus embryonic stem cells. Assady et al. (Diabetes 50:1691, 2001) identified insulin production by human embryonic stem cells differentiated to embryoid bodies, by immunohistochemistry and enzyme-linked immunoassay of the culture medium. Of course, embryoid bodies contain an enormous variety of different cell types (WO 01/51616), and Assady made no attempt to isolate the insulin-secreting cells or determine differentiation conditions that would produce enriched populations.

For embryonic stem cell derived islet cells to become a commercially viable proposition, there is a need to develop new procedures that provide for populations of islet cells of high purity.

SUMMARY

This invention provides a system for efficient production of primate cells that have differentiated from pluripotent cells into cells of the islet cell lineage. Populations of cells are described that are considerably enriched for islet progenitor cells. In turn, the islet progenitors can be further differentiated into colonies comprising cells that secrete insulin, glucagon, somatostatin, or a combination of all three.

Accordingly, one embodiment of the invention is a cell population obtained by differentiating primate pluripotent stem (pPS) cells (such as embryonic stem cells), in which at least 5% of the cells secrete at least one of the four islet cell proteins from an endogenous gene: the hormones insulin, glucagon, somatostatin, and the apparently inert product known as pancreatic polypeptide. The cells may be in clusters, comprising cells secreting each of the three endocrines, and may be processed to contain a minimum proportion of other tissue types. The cells of this invention may be identified by phenotypic markers listed later on in this disclosure. Functional efficacy can be confirmed by the ability to improve fasting glucose levels when administered to a hyperglycemic subject.

Another embodiment of the invention is a differentiated cell population capable of self-renewal, and capable of forming progeny that are mature islet cells. This means that the cells are no longer pluripotent, but retain the ability to form islet cells upon proliferation. The proportion of undifferentiated pluripotent cells in the population is preferably minimized, and any residual undifferentiated cells are not the cells responsible for forming the islet cells upon further proliferation. Optionally, replication capacity of the stem cells can be improved by increasing telomerase activity.

Another embodiment of the invention is a method for obtaining polypeptide-secreting cells, in which differentiation of pPS cells is initiated, for example, by forming embryoid bodies or other form comprising early ectoderm. The cells are then cultured in a mixture of differentiation factors, such as TGF-β antagonists like Noggin, activin A, n-butyrate, or combinations of the other factors listed below. In addition or as an alternative, the cells can be genetically altered to cause expression of a pancreatic transcription factor such as Neurogenin 3.

A further embodiment of the invention is a method of screening a compound for its ability to modulate islet cell function, using a cell composition of the invention.

Another embodiment of this invention is a method for making insulin, glucagon, or somatostatin by growing the islet cells of this invention. Also included are pharmaceutical compositions and devices containing the cells of this invention. The cells, compositions, and devices of this invention are useful for reconstituting islet cell function in a subject, especially but not limited to the treatment of Type I diabetes.

These and other embodiments of the invention are further elucidated in the description that follows.

DRAWINGS

FIG. 1 shows hES-derived hepatocytes during the differentiation and maturation process (10×, 40×). Row A shows cells 4 days after culture in medium containing 5 mM sodium n-butyrate. More than 80% of cells in the culture contain large nuclei and granular cytoplasm. The cells were switched to specialized hepatocyte culture medium for 2–4 days (Rows B and C). Multinucleated polygonal cells are common. The ES-derived hepatocytes share morphological features with freshly isolated human adult hepatocytes (Row D) and fetal hepatocytes (Row E).

Figure 2:
Figure 2:

FIG. 2 shows hES-derived cells expressing insulin. The differentiation strategy is based on the hypothesis that hepatocytes and pancreatic cells have a common early progenitor. Initial differentiation was similar to that of hepatocytes, except that cyclopamine was included in the culture medium. The cells were next cultured with the islet differentiation factors activin A, nicotinamide, cyclopamine, and a low concentration of n-butyrate. Finally, the cells were cultured for 11 days with activin A, betacellulin, nicotinamide, and IGF-1 to promote outgrowth of islet cells. DAPI stained cell nuclei are shown in the upper panel. The corresponding field in the lower panel shows diffuse red antibody staining for insulin.

Figure 3:
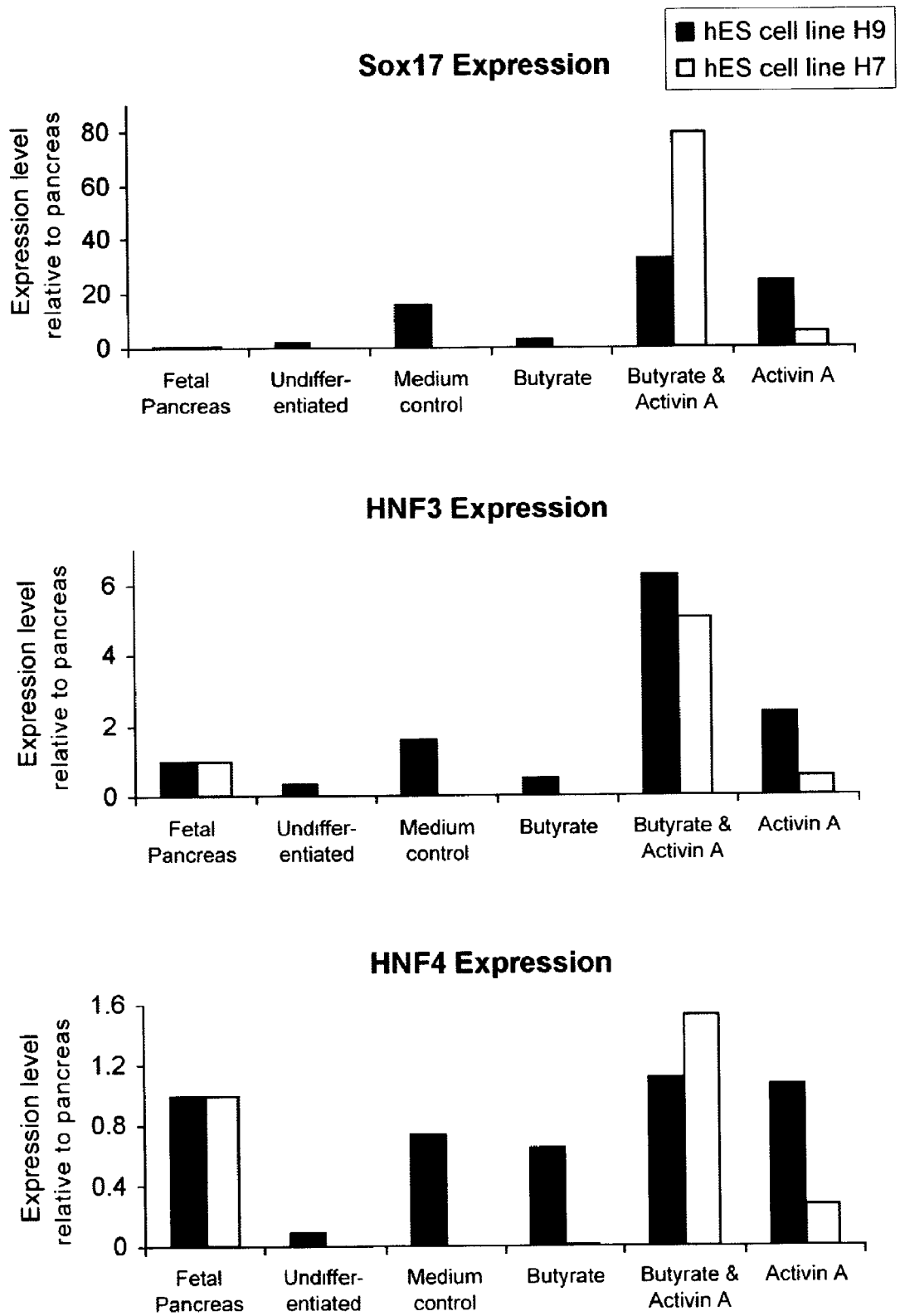

FIG. 3 shows results of a protocol in which hES cells are being directed along the pathway of islet cell ontogeny in a step-wise fashion. Expression of the three gut endoderm markers was assayed at the mRNA level, and normalized to expression levels in pancreas. Expression in undifferentiated or nonspecifically differentiated cells was low, but a combination of n-Butyrate and Activin A caused differentiation or selection of cells having characteristics for gut endoderm.

Figure 4:
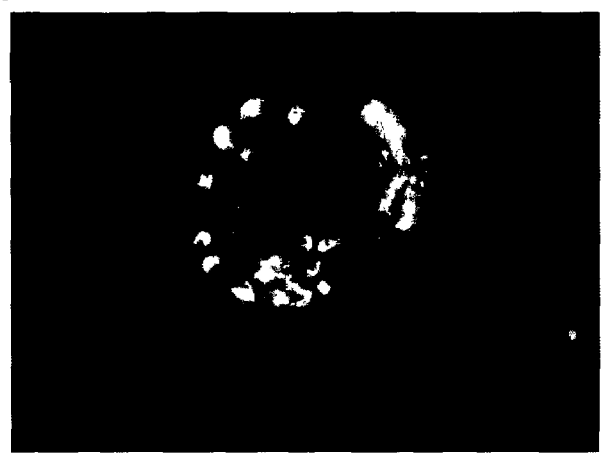
Figure 4:
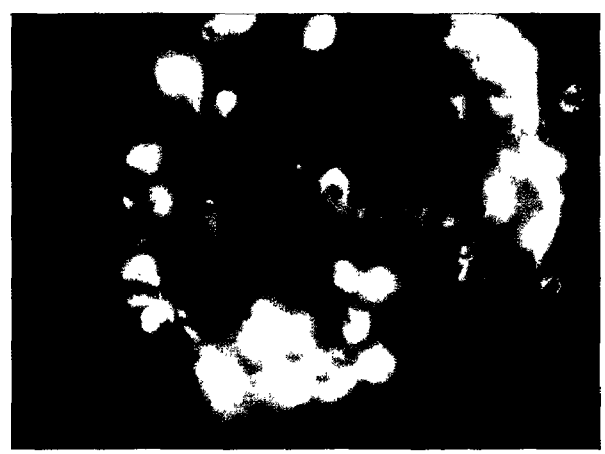
Figure 4:

FIG. 4 shows results of a protocol in which hES cells were put in long-term aggregate culture in a transition medium, and then in a medium containing mitogens and the islet cell differentiation factor Noggin. The top and middle panels show staining for insulin c-peptide at low and high magnification, indicating a cluster of mature pancreatic beta cells. The bottom panel shows staining for somatostatin, a marker of delta cells.

Figure 5:
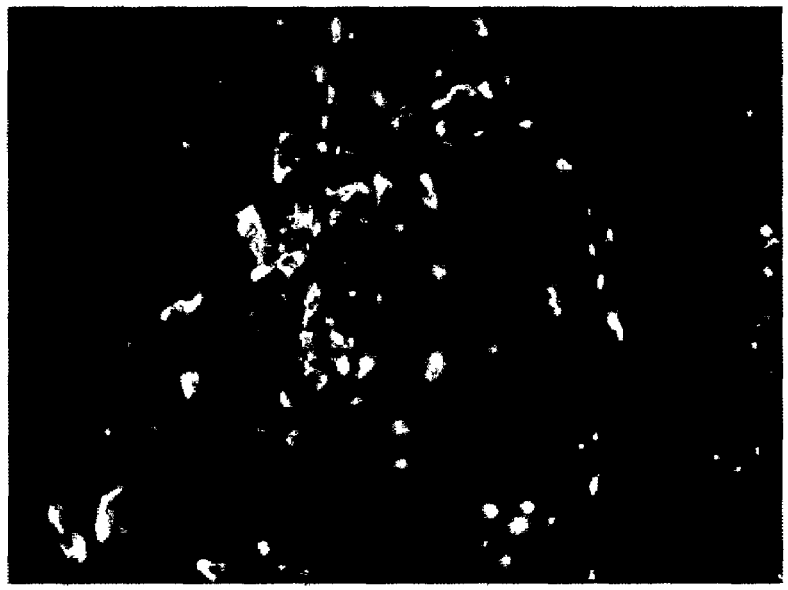
Figure 5:

FIG. 5 shows cells in an islet cell differentiation paradigm, 9 days after transfecting with a vector containing the transcription regulator gene Neurogenin 3. The cells show a high level of antibody-detectable glucagon expression.

Figure 6A:
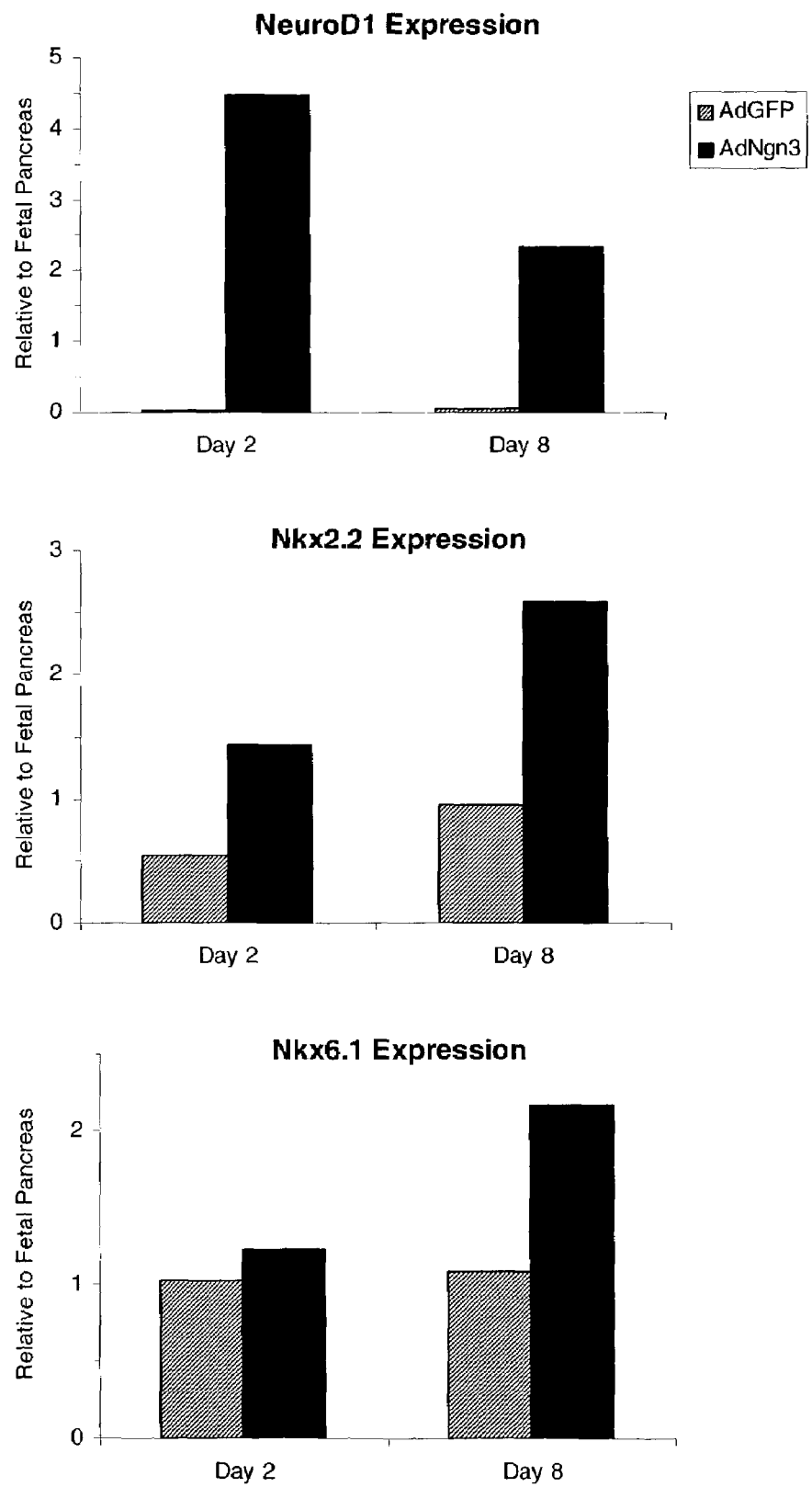
Figure 6B:
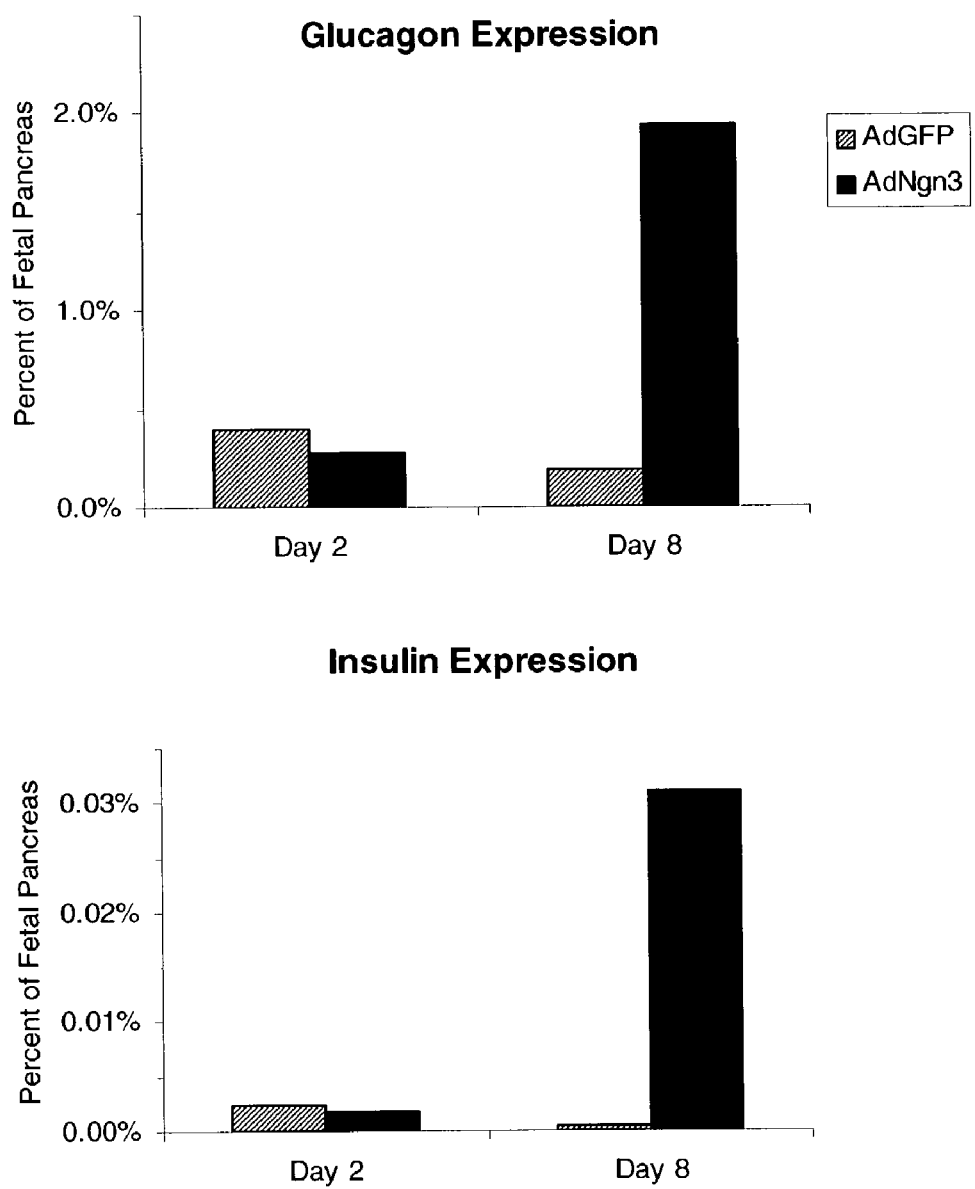

FIGS. 6(A) and (B) shows mRNA expression levels in the Neurogenin3 transduced cells (solid bars), compared with the negative control (hatched bars). The transfected gene causes upregulation downstream genes NeuroD1 and Nkx2.2 as early as day 2, leading to enhanced expression of insulin and glucagon.

DETAILED DESCRIPTION

This invention solves the problem of generating large populations of human islet cells by showing how to efficiently differentiate them from pluripotent stem cells.

It has been discovered that stem cells can be coaxed along the islet cell differentiation pathway by initiating differentiation towards the endodermal lineage, and focusing the differentiation process by culturing in the presence of factors that facilitate outgrowth of islet cells. This invention provides a system for producing a population of cells enriched for multipotent islet cell progenitors, capable of forming mature islets. If desired, the differentiation process can continue in order to maintain mature endocrine-secreting cells.

As an aid to optimizing the differentiation process, this disclosure provides a strategy of dividing the differentiation pathway into a series of sequential stages. In this way, factors effective in pushing the cells along each segment of the differentiation pathway can be identified.

In the illustration described in Example 5, the differentiation process proceeded as follows. For Stage 1, undifferentiated human embryonic stem cells from feeder free culture were differentiated so as to form a mixed cell aggregate containing endoderm cells in suspension culture. Retinoic acid was used as the initial differentiation agent, in combination with enrichment factors selenium and T3. For Stage 2, differentiation to pancreas progenitor cells was effected by culturing in a medium containing Noggin (200 ng/ml), EGF (20 ng/ml) and bFGF (2 ng/ml). For Stage 3, differentiation to end-stage islet cells was induced by withdrawing the Noggin, EGF and bFGF, and instead culturing the cells with 10 mM nicotinamide. As shown in FIG. 4, clusters of cells were obtained synthesizing antibody-detectable levels of c-peptide of insulin and somatostatin.

Methods to efficiently produce islet stem cells from pPS cells are important, because pPS cells can be caused to proliferate indefinitely. This invention provides a system that can be used to generate unbounded quantities of islet progenitors—and progeny that are committed to form mature islet cells.

The disclosure that follows provides further information on the production and testing of islet cells of this invention. It also provides extensive illustrations of how these cells can be used in research, pharmaceutical development, and the therapeutic management of conditions related to islet cell dysfunction.

Definitions

For purposes of this disclosure, the term "islet cell" refers to terminally differentiated pancreatic endocrine cells, and any precursor cell that is committed to form progeny normally classified as pancreatic endocrine. The cell expresses some of the accepted morphological features and phenotypic markers (exemplified below) that are characteristic of the islet cell lineage. Mature alpha cells secrete glucagon; mature beta cells secrete insulin; mature delta cells secrete somatostatin; PP cells secrete pancreatic polypeptide.

An "islet progenitor", "islet precursor" or "islet stem cell" is an islet cell that does not substantially secrete endocrines, but has the capability to proliferate and generate terminally differentiated cells. It may also have the capability to self-renew. Early islet progenitors are multipotent, which means that they are capable of forming at least two and potentially all four mature islet cell types.

A "pancreas progenitor", precursor, or stem cell is capable of forming both pancreatic endocrine and pancreatic exocrine cells.

In the context of cell ontogeny, the adjective "differentiated" is a relative term. A "differentiated cell" is a cell that has progressed further down the developmental pathway than the cell it is being compared with. It is a hypothesis of this invention that pluripotent embryonic stem cells in the course of normal ontogeny differentiate first to an endoderm cell that is capable of forming pancreas cells and other endoderm cell types. Further differentiation leads to the pancreatic pathway, where ~98% of the cells become exocrine, ductular, or matrix cells, and ~2% become endocrine cells. Early endocrine cells are islet progenitors, which then differentiate further into functional endocrine cells specializing in secretion of insulin, glucagon, somatostatin, or pancreatic polypeptide.

A "differentiation agent", as used in this disclosure, refers to one of a collection of compounds that are used in culture systems of this invention to produce differentiated cells of the islet lineage (including precursor cells and terminally differentiated cells). No limitation is intended as to the mode of action of the compound. For example, the agent may assist the differentiation process by inducing or assisting a change in phenotype, promoting growth of cells with a particular phenotype or retarding the growth of others. It may also act as an inhibitor to other factors that may be in the medium or synthesized by the cell population that would otherwise direct differentiation down the pathway to an unwanted cell type.

Prototype "primate Pluripotent Stem cells" (pPS cells) are pluripotent cells derived from pre-embryonic, embryonic, or fetal tissue at any time after fertilization, and have the characteristic of being capable under appropriate conditions of producing progeny of several different cell types that are derivatives of all of the three germinal layers (endoderm, mesoderm, and ectoderm), according to a standard art-accepted test, such as the ability to form a teratoma in 8–12 week old SCID mice. The term includes both established lines of stem cells of various kinds, and cells obtained from primary tissue that are pluripotent in the manner described.

Included in the definition of pPS cells are embryonic cells of various types, exemplified by human embryonic stem (hES) cells, described by Thomson et al. (Science 282:1145, 1998); embryonic stem cells from other primates, such as Rhesus stem cells (Thomson et al., Proc. Natl. Acad. Sci. USA 92:7844,1995), marmoset stem cells (Thomson et al., Biol. Reprod. 55:254, 1996) and human embryonic germ (hEG) cells (Shambloft et al., Proc. Natl. Acad. Sci. USA 95:13726, 1998). Other types of pluripotent cells are also included in the term. Any cells of primate origin that are capable of producing progeny that are derivatives of all three germinal layers are included, regardless of whether they were derived from embryonic tissue, fetal tissue, or other sources. The pPS cells are preferably not derived from a malignant source. It is desirable (but not always necessary) that the cells be karyotypically normal.

pPS cell cultures are described as "undifferentiated" when a substantial proportion of stem cells and their derivatives in the population display morphological characteristics of undifferentiated cells, clearly distinguishing them from differentiated cells of embryo or adult origin. Undifferentiated pPS cells are easily recognized by those skilled in the art, and typically appear in the two dimensions of a microscopic view in colonies of cells with high nuclear/cytoplasmic ratios and prominent nucleoli. It is understood that colonies of undifferentiated cells within the population will often be surrounded by neighboring cells that are differentiated.

"Feeder cells" are cells of one type that are co-cultured with cells of another type, to provide an environment in which the cells of the second type can grow. Certain types of pPS cells can be supported by primary mouse embryonic fibroblasts, immortalized mouse embryonic fibroblasts, or human fibroblast-like cells differentiated from hES cell. pPS cell populations are said to be "essentially free" of feeder cells if the cells have been grown through at least one round after splitting in which fresh feeder cells are not added to support growth of the pPS cells.

The term "embryoid bodies" is a term of art synonymous with "aggregate bodies", referring to aggregates of differentiated and undifferentiated cells that appear when pPS cells overgrow in monolayer cultures, or are maintained in suspension cultures. Embryoid bodies are a mixture of different cell types, typically from several germ layers, distinguishable by morphological criteria and cell markers detectable by immunocytochemistry.

A "growth environment" is an environment in which cells of interest will proliferate, differentiate, or mature in vitro. Features of the environment include the medium in which the cells are cultured, any growth factors or differentiation factors that may be present, and a supporting structure (such as a substrate on a solid surface) if present.

A cell is said to be "genetically altered" or "transfected" when a polynucleotide has been transferred into the cell by any suitable means of artificial manipulation, or where the cell is a progeny of the originally altered cell that has inherited the polynucleotide.

General Techniques

General methods in molecular genetics and genetic engineering are described in the current editions of *Molecular Cloning: A Laboratory Manual*, (Sambrook et al., Cold Spring Harbor); *Gene Transfer Vectors for Mammalian Cells* (Miller & Calos eds.); and *Current Protocols in Molecular Biology* (F. M. Ausubel et al. eds., Wiley & Sons). Cell biology, protein chemistry, and antibody techniques can be found in *Current Protocols in Protein Science* (J. E. Colligan et al. eds., Wiley & Sons); *Current Protocols in Cell Biology* (J. S. Bonifacino et al., Wiley & Sons) and *Current protocols in Immunology* (J. E. Colligan et al. eds., Wiley & Sons.). Reagents, cloning vectors, and kits for genetic manipulation referred to in this disclosure are available from commercial vendors such as BioRad, Stratagene, Invitrogen, ClonTech, and Sigma-Aldrich Co.

Cell culture methods are described generally in the current edition of *Culture of Animal Cells: A Manual of Basic Technique* (R. I. Freshney ed., Wiley & Sons); *General Techniques of Cell Culture* (M. A. Harrison & I. F. Rae, Cambridge Univ. Press), and *Embryonic Stem Cells: Methods and Protocols* (K. Turksen ed., Humana Press). Tissue culture supplies and reagents are available from commercial vendors such as Gibco/BRL, Nalgene-Nunc International, Sigma Chemical Co., and ICN Biomedicals.

Specialized works relevant to this disclosure include *The Comparative Physiology of the Pancreatic Islet*, by J. E. Brinn, Springer-Verlag 1988; *Pancreatic Islet Cell Regeneration and Growth*, by E. J. Vinik et al. eds., Kluwer 1992;; and *Immunomodulation of Pancreatic Islet (Pancreatic Islet Transplantation*, Vol 2), by R. P. Lanza et al eds., Springer Verlag 1994.

Sources of Stem Cells

This invention can be practiced using stem cells of various types. Amongst the stem cells suitable for use in this invention are primate pluripotent stem (pPS) cells derived from tissue formed after gestation, such as a blastocyst, or fetal or embryonic tissue taken any time during gestation. Non-limiting examples are primary cultures or established lines of embryonic stem cells or embryonic germ cells, as exemplified below.

The techniques of this invention can also be implemented directly with primary embryonic or fetal tissue, deriving islet cells directly from primary cells that have the potential to give rise to islet cells without first establishing an undifferentiated cell line. Under certain circumstances, the methods of this invention may also be invoked using multipotent cells from cord blood, placenta, or certain adult tissues.

Embryonic Stem Cells

Embryonic stem cells can be isolated from blastocysts of members of the primate species (U.S. Pat. No. 5,843,780; Thomson et al., Proc. Natl. Acad. Sci. USA 92:7844, 1995). Human embryonic stem (hES) cells can be prepared from human blastocyst cells using the techniques described by Thomson et al. (U.S. Pat. No. 6,200,806; Science 282:1145, 1998; Curr. Top. Dev. Biol. 38:133 ff., 1998) and Reubinoff et al, Nature Biotech. 18:399, 2000. Equivalent cell types to hES cells include their pluripotent derivatives, such as primitive ectoderm-like (EPL) cells, as outlined in WO 01/51610 (Bresagen). hES cells can be obtained from human preimplantation embryos. Alternatively, in vitro fertilized (IVF) embryos can be used, or one-cell human embryos can be expanded to the blastocyst stage (Bongso et al., Hum Reprod 4: 706, 1989). Embryos are cultured to the blastocyst stage in G1.2 and G2.2 medium (Gardner et al., Fertil. Steril. 69:84, 1998). The zona pellucida is removed from developed blastocysts by brief exposure to pronase (Sigma). The inner cell masses are isolated by immunosurgery, in which blastocysts are exposed to a 1:50 dilution of rabbit anti-human spleen cell antiserum for 30 min, then washed for 5 min three times in DMEM, and exposed to a 1:5 dilution of Guinea pig complement (Gibco) for 3 min (Solter et al., Proc. Natl. Acad. Sci. USA 72:5099,1975). After two further washes in DMEM, lysed trophectoderm cells are removed from the intact inner cell mass (ICM) by gentle pipetting, and the ICM plated on mEF feeder layers.

After 9 to 15 days, inner cell mass-derived outgrowths are dissociated into clumps, either by exposure to calcium and magnesium-free phosphate-buffered saline (PBS) with 1 mM EDTA, by exposure to dispase or trypsin, or by mechanical dissociation with a micropipette; and then replated on mEF in fresh medium. Growing colonies having undifferentiated morphology are individually selected by micropipette, mechanically dissociated into clumps, and replated. ES-like morphology is characterized as compact colonies with apparently high nucleus to cytoplasm ratio and prominent nucleoli. Resulting ES cells are then routinely split every 1–2 weeks by brief trypsinization, exposure to Dulbecco's PBS (containing 2 mM EDTA), exposure to type IV collagenase (~200 U/mL; Gibco) or by selection of individual colonies by micropipette. Clump sizes of about 50 to 100 cells are optimal.

Embryonic Germ Cells

Human Embryonic Germ (hEG) cells can be prepared from primordial germ cells present in human fetal material taken about 8–11 weeks after the last menstrual period. Suitable preparation methods are described in Shamblott et al., Proc. Natl. Acad. Sci. USA 95:13726,1998 and U.S. Pat. No. 6,090,622.

Briefly, genital ridges processed to form disaggregated cells. EG growth medium is DMEM, 4500 mg/L D-glucose, 2200 mg/L mM $NaHCO_3$; 15% ES qualified fetal calf serum (BRL); 2 mM glutamine (BRL); 1 mM sodium pyruvate (BRL); 1000–2000 U/mL human recombinant leukemia inhibitory factor (LIF, Genzyme); 1–2 ng/mL human recombinant bFGF (Genzyme); and 10 μM forskolin (in 10% DMSO). Ninety-six well tissue culture plates are prepared with a sub-confluent layer of feeder cells (e.g., STO cells, ATCC No. CRL 1503) cultured for 3 days in modified EG growth medium free of LIF, bFGF or forskolin, inactivated with 5000 rad γ-irradiation. ~0.2 mL of primary germ cell (PGC) suspension is added to each of the wells. The first passage is done after 7–10 days in EG growth medium, transferring each well to one well of a 24-well culture dish previously prepared with irradiated STO mouse fibroblasts. The cells are cultured with daily replacement of medium until cell morphology consistent with EG cells is observed, typically after 7–30 days or 1–4 passages.

Propagation of pPS Cells in an Undifferentiated State pPS cells can be propagated continuously in culture, using culture conditions that promote proliferation without promoting differentiation. Exemplary serum-containing ES medium is made with 80% DMEM (such as Knock-Out DMEM, Gibco), 20% of either defined fetal bovine serum (FBS, Hyclone) or serum replacement (WO 98/30679), 1% non-essential amino acids, 1 mM L-glutamine, and 0.1 mM β-mercaptoethanol. Just before use, human bFGF is added to 4 ng/mL (WO 99/20741, Geron Corp.). Traditionally, ES cells are cultured on a layer of feeder cells, typically fibroblasts derived from embryonic or fetal tissue.

Scientists at Geron have discovered that pPS cells can be maintained in an undifferentiated state even without feeder cells. The environment for feeder-free cultures includes a suitable culture substrate, particularly an extracellular matrix such as Matrigel® or laminin. Typically, enzymatic digestion is halted before cells become completely dispersed (say, ~5 min with collagenase IV). Clumps of ~10 to 2,000 cells are then plated directly onto the substrate without further dispersal.

Feeder-free cultures are supported by a nutrient medium containing factors that support proliferation of the cells without differentiation. Such factors may be introduced into the medium by culturing the medium with cells secreting such factors, such as irradiated (~4,000 rad) primary mouse embryonic fibroblasts, telomerized mouse fibroblasts, or fibroblast-like cells derived from pPS cells. Medium can be conditioned by plating the feeders at a density of ~$5-6 \times 10^4$ cm$^{-2}$ in a serum free medium such as KO DMEM supplemented with 20% serum replacement and 4 ng/mL bFGF. Medium that has been conditioned for 1–2 days is supplemented with further bFGF, and used to support pPS cell culture for 1–2 days. Features of the feeder-free culture method are further discussed in International Patent Publication WO 01/51616; and Xu et al., Nat. Biotechnol. 19:971, 2001.

Under the microscope, ES cells appear with high nuclear/cytoplasmic ratios, prominent nucleoli, and compact colony formation with poorly discernable cell junctions. Primate ES cells express stage-specific embryonic antigens (SSEA) 3 and 4, and markers detectable using antibodies designated Tra-1-60 and Tra-1-81 (Thomson et al., Science 282:1145, 1998). Mouse ES cells can be used as a positive control for SSEA-1, and as a negative control for SSEA-4, Tra-1-60, and Tra-1-81. SSEA-4 is consistently present on human embryonal carcinoma (hEC) cells. Differentiation of pPS cells in vitro results in the loss of SSEA-4, Tra-1-60, and Tra-1-81 expression, and increased expression of SSEA-1, which is also found on undifferentiated hEG cells.

Materials and Procedures for Preparing Islet Cells and their Derivatives

Islet cells of this invention are obtained by culturing, differentiating, or reprogramming stem cells in a special growth environment that enriches for cells with the desired phenotype (either by outgrowth of the desired cells, or by inhibition or killing of other cell types). These methods are applicable to many types of stem cells, including primate pluripotent stem (pPS) cells described in the previous section.

Step-wise Differentiation

It is a hypothesis of the invention that the production and enrichment of islet cells from pPS cells may be facilitated by forming an early-stage progenitor that is multipotential for formation of pancreatic cells and other cell types. In a general sense, this strategy involves first forming a cell population enriched for a relevant committed common precursor cell, and then further differentiating into more mature cells that are more and more specialized towards the formation of islets. According to this strategy, differentiation of pPS cells towards mature islets is done in several deliberate stages.

One intermediate between undifferentiated pPS cells and mature islets is an immature endoderm cell. Early in ontogeny, endoderm cells are capable of making epithelial cells of the GI tract and respiratory system, and the key digestive organs (liver and pancreas). Islet cells can be generated using a two-stage approach. Stage 1 involves obtaining a population of common endoderm precursor cells. Stage 2 involves maturing the endoderm precursors into pancreatic endocrine. As illustrated in Example 3, pPS cells can be initiated along the endoderm differentiation pathway by culturing with the hepatocyte differentiation agent n-butyrate. Further elaboration of the hepatocyte differentiation paradigm is described in International Patent Publication WO 01/81549 (Geron Corporation). Sonic Hedgehog is thought to be involved in liver specification, so including cyclopamine (an inhibitor of Sonic Hedgehog) in the culture medium is thought to help divert the cells toward the pancreatic lineage. Differentiation can then be pushed further in a subsequent step, using the terminal differentiation factor nicotinamide (in the presence of cyclopamine and activin A).

In a further manifestation of this approach, the differentiation pathway is divided into three stages. pPS cells are first differentiated to endoderm (Stage 1), and then to a second intermediate (Stage 2)—say, the level of a committed pancreas precursor (identifiable with the marker Pdx1). A further differentiation step (Stage 3) can be performed if the user wants to obtain mature islets. By way of illustration, to accomplish Stage I, pPS cells can be differentiated to cells having markers for gut endoderm using a combination of n-butyrate and activin A (Example 4). Alternatively, a heterogeneous population comprising endodermal cells can be prepared by culturing pPS cells with retinoic acid in the presence of enriching agents (selenium and thyroid hormones such as T3) (Example 5). To accomplish Stage 2, the cells can be cultured with TGF-β antagonists such as Noggin, in combination with mitogens (a member of the FGF family, possibly in combination with EGF or betacellulin) (Example 5). It may also be helpful to block hedgehog signaling with cyclopamine. Stage 3 can be accomplished as already described, using nicotinamide as the terminal differentiation agent (Example 5). Alternatively, transcription factors can be activated by direct manipulation that causes progression from Pdx1 positive pancreatic precursors to mature islet cells (Example 6).

This step-wise approach to differentiation is intended as a guide to the reader, and does not limit the invention except where explicitly indicated. The differentiation pathway can be broken down into even more stages so that step-wise differentiation can be optimized in an incremental fashion. For example, a potential intermediate between pancreatic precursors and mature islets are precursor cells committed to form pancreatic endocrine. On the other hand, depending on the circumstances, effective differentiation agents may be combined to work on cells in different stages at the same time, or to promote a cascading effect down the differentiation pathway.

The desired end-stage cell population will depend in part on its intended use. For example, committed islet progenitor cells may be of particular value for therapy of generalized islet insufficiency, and studying islet differentiation in vitro.

Earlier progenitors may have greater capacity for self-renewal. Mature cell populations showing high-level synthesis of insulin or other endocrines where immediate production of the hormone is required. The differentiation process is tailored accordingly, stopping the process at a stage that yields the desired level of maturation.

The following sections provide tissue culture and gene transfection techniques that are effective in promoting differentiation in the manner described.

Initiating the Differentiation Process

There are two approaches to begin differentiation of pPS cells towards endodermal cells. One is to plate the cells onto a new substrate, or exchange the medium to remove extracellular matrix or soluble factors that inhibit differentiation. This is sometimes referred to as the "direct differentiation method", and is described in general terms in International patent publication WO 01/51616, and U.S. patent Publication 20020019046. It is usually preferable in the direct differentiation method to begin with a feeder-free culture of pPS cells, so as to avoid potential complications in the differentiation process caused by residual feeder cells. Example 4 provides an illustration in which gut endoderm is produced by direct differentiation by introducing medium containing early differentiation factors.

The other approach is to put undifferentiated pPS cells in suspension culture, which will frequently cause them to form embryoid bodies or aggregates. For example, pPS cells are harvested by brief collagenase digestion, dissociated into clusters, and passaged in non-adherent cell culture plates. The aggregates are fed every few days, and then harvested after a suitable period, typically 4–8 days (Examples 1 & 5). In some instances, differentiation is enhanced by other factors in the medium: for example, retinoic acid (Example 5) or dimethyl sulfoxide (DMSO). Depending on the conditions, aggregates will generally start by forming a heterogeneous population of cell types, including a substantial frequency of endoderm cells. The embryoid bodies can then be dispersed and replated for the next stage in the differentiation process, on substrates such as laminin or fibronectin; or passaged in suspension culture, using non-adherent plates and a suitable medium.

Direct differentiation or differentiation in aggregates can be monitored for the presence of endoderm cells using the markers listed below. Once a sufficient proportion of endoderm is obtained, cells are replated or otherwise manipulated to begin Stage II. In certain circumstances, differentiation or maintenance of islet cells may be enhanced if the cells are kept in micromass clusters (for example, 50 to 5,000 cells), so that alpha, beta, and delta cells can interact directly.

Once the common progenitor cells are made in this manner, they can be cultured with specific differentiation factors and/or induced with islet-specific genes or promoters as described in the sections that follow.

Driving Differentiation Further Towards Islet Cells Using Soluble Factors In order to drive the culture further down the stages of the islet pathway, pPS cells or their differentiated progeny may be cultured in a cocktail of islet differentiation factors. Alone or in combination, each of the factors may increase the frequency of conversion to the desired cell type, cause outgrowth of cells with a islet phenotype, inhibit growth of other cell types, or enrich for islet cells in another fashion. It is not necessary to understand the mechanism resulting in islet cells being enriched in order to practice the invention. What follows is a non-limiting list of candidate differentiation factors.

TABLE 1

Factors for Differentiation of Islet Cells from pPS Cells

| Factor | Compound type or family | Proposed function | Initial working concentration |
|---|---|---|---|
| Cyclopamine | steroidal alkaloid | inhibitor of hedgehog signaling; may also act as inhibitor of cholesterol biosynthesis | 10 µM |
| Betacellulin | EGF family member | mitogen and promoter of beta cell differentiation. These two functions have been ascribed to different domains of the protein | 4 nM |
| Activin A | TGF-β family member | differentiation factor, causes ductallike cell lines to differentiate into endocrine pancreas cells | 4 nM |
| Exendin-4 | glucagon-like peptide 1 agonist | More stable form of GLP-1 (see below) | 20 nM |
| Glucagon-like peptide 1 (GLP1) | peptide hormone, one of the protein products from the glucagon gene; G-protein coupled receptor ligand | induces glucose production, insulin secretion, induces beta cell neogenesis, induced beta cell proliferation | 20 nM |
| Hepatocyte Growth Factor (HGF) | Ligand for the c-Met receptor | Increases beta cell mass in transgenic animals over-expressing HGF, induces beta cell formation from ductal cell line | 10 ng/ml |
| Niacinamide (nicotinamide) | Member of vitamin B family | May affect ADP-ribosylation and/or oxidation state of cell; promotes beta cell differentiation | 10 mM |
| Insulin-like growth factor 1 (IGF-I) | Peptide hormone | Beta cell mitogen | 10 nM |
| n-butyrate | | Histone deacetylase inhibitor (used to produce hepatocytes) | 0.5 mM to 2.5 mM |
| Retinoic Acid (all trans) | Retinoids | differentiation factor | 10 µM |
| Growth Hormone (Human pituitary Somatotropin) | somatotropin/ prolactin family | beta cell mitogen | 100 ng/ml |
| Placental Lactogen | somotropin/ prolactin family | Increases beta cell mass in transgenic animals over-expressing PL, beta cell mitogen during pregnancy | 50 ng/ml |
| Vascular endothelial growth factor (VEGF) | Flt-1 and Flk-1 are receptors. PDGF/VEGF family | possible mitogen for endothelial islet precursor | 50 ng/ml |
| Insulin-like growth factor II (IGF-II) | insulin family | similar to IGF-1, mitogen, not as strongly implicated in pancreas development or function | 10 nM |

TABLE 1-continued

Factors for Differentiation of Islet Cells from pPS Cells

| Factor | Compound type or family | Proposed function | Initial working concentration |
|---|---|---|---|
| 3-Isobutyl-1-methyl-xanthine (IBMX) | phosphodi-esterase inhibitor, increases cAMP levels | increases insulin secretion | 100 µM |
| wortmannin | PI-3 kinase inhibitor | may increase insulin secretion | 30 nM |
| Gastrin | Peptide hormone | May promote beta cell neogenesis | 10 ng/ml |
| Cholecysto-kinin | Gut hormone | May aid in maturation of islets | 5 µM |
| Nerve growth factor (NGF) | NGF family | increases insulin secretion | 50 ng/ml |
| Epidermal growth factor (EGF) | EGF family (see beta-cellulin above) | transgenic over-expression results in proliferation of beta cells | 4 nM |
| Keratinocyte growth factor (KGF), aka FGF7 | FGF family member | transgenic over-expression results in proliferation of beta cells | 10 ng/ml |
| Platelet-derived growth factor (PDGF) | PDGF family (see VEGF above) | potential precursor mitogen | 50 ng/ml |
| Regenerating gene (Reg) | Reg family | Plays a role in islet regeneration after pancreas damage | 100 ng/ml |
| Islet neogenesis-associated protein (INGAP) | Reg family | May play a role in islet regeneration | 100 ng/ml |

Other ligands or antibodies that bind the same receptors can be considered equivalents to any of the receptor ligands referred to in this disclosure.

Typically, at least two, three, or more than three such factors are combined in the differentiation cocktail. Human proteins are preferred, but species homologs and variants may also be used. In place of any of these factors, the reader may use other ligands that bind the same receptors or stimulate the same signal transduction pathways, such as receptor-specific antibody. In addition, other components may be included in the medium to neutralize the effect of other factors that may be present to drive differentiation down a different pathway.

The efficacy of any of these factors can be determined empirically using a matrix strategy to arrive at combinations capable of promoting differentiation one or more steps down the islet cell pathway. Efficacy is assessed by monitoring emergence of the phenotype of the intended intermediate or end-stage cell, using the phenotypic markers such as those listed below. For example, factors believed to induce endocrine pancreas differentiation or proliferation are tested for their ability to induce Pdx1 expression and subsequently and insulin expression in standard culture conditions.

A fractional factorial design strategy can be used to screen several compounds in an efficient manner. Each factor is assigned two levels: for example, the culture matrix would be assigned fibronectin for one level and laminin for the second level. In 64 factor combinations (64 experiments), it is possible to determine which factors (from a group of 15–20) significantly influence differentiation in a statistically robust manner. Combinations suitable for analysis by this strategy include cyclopamine, TGF family members (TGF-α, Activin A, Activin B, TGFβ1, TGFβ3), Exendin 4, nicotinamide, n-butyrate, DMSO, all-trans retinoic acid, GLP-1, bone morphogenic proteins (BMP-2, BMP-5, BMP-6, BMP-7), insulin-like growth factors (IGF-I, IGF-II), fibroblast growth factor (FGF7, FGF10, bFGF, FGF4), other growth factors (EGF, betacellulin, growth hormone, HGF), other hormones (prolactin, cholecytokinin, gastrin I, placental lactogen), TGF-β family antagonists (Noggin, follistatin, chordin), IBMX, wortmannin, dexamethazone, Reg, INGAP, cAMP or cAMP activators (forskolin), and extracellular matrix components (laminin, fibronectin). The emerging cell populations are assessed by phenotypic markers, and expression patterns are analyzed to determine which factors have a positive or negative influence on the differentiation pathway.

Directing or Monitoring Differentiation Using Genetically Modified Cells

In optimizing a differentiation or separation strategy, it is sometimes helpful to use cells that have been genetically altered with a vector in which a tissue-specific promoter drives expression of a reporter gene.

Suitable promoters specific for islet progenitors include those driving transcription of Pdx1 (NT_009799), Neurogenin 3 (NT_008583), NeuroD1 (NT_005265), Nestin (NT_004858) and Pft1a-p48 (NT_008705). Suitable promoters specific for mature islet cells are those driving expression of insulin (GenBank Accession NT_009308), glucagon (NT_022154), somatostatin (NT_005962), or pancreatic polypeptide (NT_010755). A minimal effective sequence of the chosen promoter (~0.5 to 5 kB of upstream sequence) is amplified by PCR and spliced into a standard plasmid, adenovirus, lentivirus, or retrovirus vector, in a position that drives expression of a suitable reporter gene. Suitable reporter genes either encode a fluorescent molecule (such as green fluorescent protein or luciferase), encode a detectable enzyme (such as alkaline phosphatase), or produce a cell surface antigen (any heterologous protein or carbohydrate) that can be detected by antibody or lectin binding.

Cells transfected with a tissue-specific promoter can be used to optimize differentiation procedures in the manner already described. For example, transfected undifferentiated pPS cells or cells in the early stage of differentiation can be subject to various differentiation regimes, and then analyzed for the proportion of cells reporting expression driven by the islet-specific promoter. This provides a rapid read-out of effective differentiation agents, culture environments, and timing. The optimal procedure can then be used with untransfected cells to generate high-quality populations of the islet lineage that have a native genotype.

Cells transfected with a tissue-specific promoter can also be used as a means for accomplishing mechanical sorting. For example, the promoter may drive expression of a drug-resistant phenotype, such as the neomycin resistance gene (conferring resistance to the drug G418) or the blasticidin resistance gene. In this case, once the cells are differentiated, they are cultured with the drug to promote outgrowth of the desired cell type. Alternatively, the reporter gene may encode a fluorescent molecule, or cause expression of a detectable surface antigen. In this case, cells of interest are sorted from a population of differentiated cells by cell sorting based on either direct or indirect fluorescence, or by immunoadsorption. A non-replicative, non-integrating vector (such as an adenovirus vector) can be used for transient transfection during the sorting step, and will dilute out upon subsequent proliferation of the cell, leaving the cell with a native genotype.

The cells can also be genetically altered for the purpose of directly driving the cells further down the differentiation pathway for islet cells or their progenitors. It is hypothesized that deliberate up-regulation of certain genes normally expressed in the islet cells will cause less differentiated cells to recruit the genetic expression profile appropriate for more mature islet cells. Suitable genes include those that encode transcription regulators capable of influencing downstream gene expression. Candidates for pancreatic ontogeny (roughly in order of their position in the pathway) include Sox17 (GenBank Accession NM_022454), HIxb9 (NM_005515), Pdx1 (NM_000209), Neurogenin3 (NM_020999), Pax4 (NM_006193) or NeuroD1 (NM_002500), Is1 (NM_002202), Nkx2.2 (NM_002509), and Nkx6.1 (NM_006168).

An illustration of this approach is provided in Example 6. Neurogenin 3 expression induced by transduction of cells in an islet cell differentiation paradigm enhances expression in downstream regulatory genes, and genes encoding islet hormones. The neurogenins are a family of a neuroD-related bHLH transcription factors: neuronal determination genes active in the developing nervous system.

Characteristics of Differentiated Cells

Cells can be characterized according to phenotypic criteria, such as microscopic observation of morphological features, detection or quantitation of expressed cell markers, functional criteria measurable in vitro, and behavior upon infusion into a host animal.

Phenotypic Markers

Cells of this invention can be characterized according to whether they express phenotypic markers characteristic of islet cells of various kinds. Useful markers include those shown in Table 2.

TABLE 2

| Phenotypic Markers for Cell Identification | |
|---|---|
| SSEA-4 | Embryonic stem and germ cells |
| Oct-4 | Undifferentiated embryonic pluripotent cells |
| Telomerase reverse transcriptase (TERT) | Cells capable of unlimited replication (e.g., undifferentiated pPS cells) |
| Pdx1 | expressed before pancreatic bud formation in the region of the duodenum that give rise to the pancreas. Also expressed in mature beta cells |
| Neurogenin 3 (Ngn3) | marker of islet precursor cells. |
| Glucagon | alpha cells |
| Nkx6.1 | beta cell marker |
| glucokinase | beta cell marker |
| Insulin or proinsulin | mature beta cells |
| Somatostatin | delta cells |
| pancreatic polypeptide | PP cells |
| islet amyloid polypeptide (IAPP) | islet marker |
| Islet-1 | islet marker, also neural expression |
| Beta-2/NeuroD | pan islet cell marker |
| HNF3b | endoderm marker |
| HNF4a | endoderm marker |
| Sox17 | definitive endoderm marker |
| Amylase | exocrine cells |
| HES | exocrine pancreas marker |
| nestin | potential precursor cell marker |
| Sonic hedgehog | signaling molecule, absence is required for pancreas formation |
| CK19 | pancreatic duct marker (possible pancreatic precursor) |

TABLE 2-continued

| Phenotypic Markers for Cell Identification | |
|---|---|
| Glut-2 | glucose transporter |
| Patched homologue | hedgehog receptor |
| Smoothened homologue | hedgehog receptor |

Tissue-specific markers can be detected using any suitable immunological technique—such as flow immunocytochemistry for cell-surface markers, or immunohistochemistry (for example, of fixed cells or tissue sections) for intracellular or cell-surface markers. A detailed method for flow cytometry analysis is provided in Gallacher et al., Blood 96:1740, 2000. Expression of a cell-surface antigen is defined as positive if a significantly detectable amount of antibody will bind to the antigen in a standard immunocytochemistry or flow cytometry assay, optionally after fixation of the cells, and optionally using a labeled secondary antibody or other conjugate to amplify labeling. Current sources of specific antibody include the following: Insulin, Sigma Aldrich (12018); glucagon, Sigma Aldrich (G2654); somatostatin, Santa Cruz Biotech (sc-7820); neurogenin 3, Chemicon (AB5684); nestin, BD Transduction Labs (N17220); α-amylase, Sigma Aldrich (A8273); Glut-2, Alpha Diagnostics (GT-22A)

The expression of tissue-specific gene products can also be detected at the mRNA level by Northern blot analysis, dot-blot hybridization analysis, or by reverse transcriptase initiated polymerase chain reaction (RT-PCR) using sequence-specific primers in standard amplification methods. See U.S. Pat. No. 5,843,780 for further details. Sequence data for particular markers listed in this disclosure can be obtained from public databases such as GenBank.

Amplification probe/primer combinations suitable for use in amplification assays include the following: Ins (GenBank NM_000207): primers CAGCCTTTGT GAACCAACACC (SEQ. ID NO:1); CGTTCCCCG CACACTAGGTA (SEQ. ID NO:2); probe CGGCTCACA CCTGGTGGA AGCTC (SEQ. ID NO:3). Nkx6.1 (NM_006168): primers CTGGAGGG ACGCACGC (SEQ. ID NO:4); TCCCGTCTT TGTCCAACAAAA (SEQ. ID NO:5); probe TGGCCTGT ACCCCTCATC AAGGATCC (SEQ. ID NO:6). Pdx1 (NM_000209): primers TGGCGTTGT TTGTGGCTG (SEQ. ID NO:7); AGGTCCCAA GGTGGAGTGC (SEQ. ID NO:8); probe TGCGCA CATCCCTGCCC TCCTAC. Ngn3 (NM_020999): primers TCTCTATTCT TTTGCGCCGG (SEQ. ID NO:10); CTTGGACAG TGGGCGCAC (SEQ. ID NO:11); probe AGAAAG GATGACGCCTCAA CCCTCG (SEQ. ID NO:12). IAPP (NM_000415): primers AAGGCAGGA GAATCGCTTGA (SEQ. ID NO:13); TGGTGCAAT CTCGGCTCA (SEQ. ID NO:14); probe CCCAGG AGGCGGAG GTTGCA (SEQ. ID NO:15).

HNF3b (NM_021784): primers CCGACTGGAG CAGCTACTATG (SEQ. ID NO:16); TACGTGTTCA TGCCGTTCAT (SEQ. ID NO:17); probe CAGAGCCCGA GGGCTACTCC TCC (SEQ. ID NO:18). p48 (XM_166107): primers CAGGCCCAGA AGGTCATC (SEQ. ID NO:19); GGGAGGGAGG CCATAATC (SEQ. ID NO:20); probe ATCTGCCATC GGGGCACCC (SEQ. ID NO:21). HNF6 (XM_030712): primers AATACCAAAG AGGTGGCGCA (SEQ. ID NO:22); ATGGCCTGTG GGATGCTGT (SEQ. ID NO:23); probe CGTATCACCA CCGAGCTCAA GCGC (SEQ. ID NO:24). glucagon (NM_002054): primers GCTGCCAAGG AATTCATTGC (SEQ. ID NO:25); CTTCAACAAT GGCGACCTCTTC (SEQ. ID NO:26);

probe TGAAAGGCCG AGGAAGGCGA GATT (SEQ. ID NO:27). HNF6 (NM_030712): primers GCTGGGGTGA CCTCAATCTA (SEQ. ID NO:28); CAGGAACCTG CAT-GAGGACT (SEQ. ID NO:29); probe AGTTTCAGAG CCATTGGGCG GTG (SEQ. ID NO:30). NeuroD1 (NM_002500): primers TCACTGCTCA GGACCTACTAACA (SEQ. ID NO:31); GAGGACCTTG GGGCTGAG (SEQ. ID NO:32); probe TACAGCGAGA GTGGGCTGAT GGG (SEQ. ID NO:33). HNF4a (NM_000457): primers GAGATCCATG GTGTTCAAGGA (SEQ. ID NO:34); GTCAAGGATG CGTATGGACA (SEQ. ID NO:35); probe CTACATTGTC CCTCGGCACT GCC (SEQ. ID NO:36). Sox17 (NM_022454): primers CAGCAGAATC CAGAC-CTGCA (SEQ. ID NO:37); GTCAGCGCCT TCCACGACT (SEQ. ID NO:38); probe ACGCCGAGTT GAGCAAGATG CTGG (SEQ. ID NO:39). HIxb9 (NM_005515): primers GCCACCTCGC TCATGCTC (SEQ. ID NO:40); CCATTTCATC CGCCGGTTC (SEQ. ID NO:41); probe CCGAGACCCA GGGAAGATTT GGTTCC (SEQ. ID NO:42). Nkx2.2 (NM_002509): primers CGAGGGCCTT CAGTACTCC (SEQ. ID NO:43); TTGTCATTGT CCGGT-GACTC (SEQ. ID NO:44); probe ACTCAAGCTC CAAGTCCCCG GAG (SEQ. ID NO:45).

Initial assessment can be done using a marker combination that provides a wide ontogenic profile: for example, Pdx1 for early pancreas cells; Ngn3 for early pancreatic endocrine cells; and insulin for mature beta cells. The cells are harvested from the differentiation paradigms described earlier at regular intervals (say, weekly) to determine the kinetics of differentiation. Cells that test positive for these markers can then be analyzed for expression of other markers, such as IAPP and Nkx6.1. Once the cells are characterized, differentiation factor combinations and the timing of each step can be optimized.

Certain embodiments of this invention relate to populations in which at least 2%, 5%, 10%, or more of the cells bear the surface markers referred to above, either alone or in combination. Endocrine function is critical to many research and therapeutic applications, in which case populations comprising at least 5% of the cells secreting insulin, glucagon, somatostatin, or pancreatic polypeptide are of particular interest, as are progenitor cells capable of differentiating into such endocrine-secreting cells. It is a hypothesis of this invention that interaction between the alpha, beta, and delta cells may be important in preventing dedifferentiation and maintaining efficient endocrine secretion. This invention also includes masses or clusters of cells (perhaps 50–5,000 cells in size), containing two or three of these cell types, either bound in a matrix of their own making, with a matrix component supplied in culture, or by microencapsulation.

Also desirable are populations with a low residual proportion of undifferentiated pPS cells. Preferred populations are less than 1%, or 0.2% SSEA-4+ve, Oct-4+ve, or positive for expression of endogenous telomerase reverse transcriptase. Preferred populations also have relatively low proportions (<5%, 1%, or 0.2%) of certain other cell types, such as hepatocytes (albumin positive cells), skeletal muscle cells (myoD positive), smooth muscle cells (smooth muscle actin), cells with fibroblast morphology, or neurons (β-tubulin III or NCAM positive cells).

When derived from an established line of pPS cells, the cell populations and isolated cells of this invention will have the same genome as the line from which they are derived. This means that over and above any karyotype abnormalities, the chromosomal DNA will be over 90% identical between the pPS cells and the islet cells, which can be inferred if the islet cells are obtained from the undifferentiated line through the course of normal mitotic division. Islet cells that have been treated by recombinant methods to introduce a transgene or knock out an endogenous gene are still considered to have the same genome as the line from which they are derived, since all non-manipulated genetic elements are preserved.

Animal Model Experiments

Of considerable interest for the purposes of islet cells for clinical application is the ability of cell populations to reconstitute the islet system of a host animal. Reconstitution can be tested using several well-established animal models.

The non-obese diabetic (NOD) mouse carries a genetic defect that results in insulitis showing at several weeks of age (Yoshida et al., Rev. Immunogenet. 2:140, 2000). 60–90% of the females develop overt diabetes by 20–30 weeks. The immune-related pathology appears to be similar to that in human Type I diabetes. Other models of Type I diabetes are mice with transgene and knockout mutations (Wong et al., Immunol. Rev. 169:93, 1999). A rat model for spontaneous Type I diabetes was recently reported by Lenzen et al. (Diabetologia 44:1189, 2001). Hyperglycemia can also be induced in mice (>500 mg glucose/dL) by way of a single intraperitoneal injection of streptozotocin (Soria et al., Diabetes 49:157, 2000), or by sequential low doses of streptozotocin (Ito et al., Environ. Toxicol. Pharmacol. 9:71, 2001). To test the efficacy of implanted islet cells, the mice are monitored for return of glucose to normal levels (<200 mg/dL).

Larger animals provide a good model for following the sequelae of chronic hyperglycemia. Dogs can be rendered insulin-dependent by removing the pancreas (J. Endocrinol. 158:49, 2001), or by feeding galactose (Kador et al., Arch. Opthalmol. 113:352, 1995). There is also an inherited model for Type I diabetes in keeshond dogs (Am. J. Pathol. 105:194, 1981). Early work with a dog model (Banting et al., Can. Med. Assoc. J. 22:141, 1922) resulted in a couple of Canadians making a long ocean journey to Stockholm in February of 1925.

By way of illustration, a pilot study can be conducted using pPS derived islet cells in the following animals: a) non-diabetic nude (T-cell deficient) mice; b) nude mice rendered diabetic by streptozotocin treatment; and c) nude mice in the process of regenerating islets following partial pancreatectomy. The number of cells transplanted is equivalent to ~1000–2000 normal human islets, implanted under the kidney capsule, in the liver, or in the pancreas. For non-diabetic mice, the endpoints of can be assessment of graft survival (histological examination) and determination of insulin production by biochemical analysis, RIA, ELISA, and immunohistochemistry. Streptozotocin treated and partially pancreatectomized animals can also be evaluated for survival, metabolic control (blood glucose) and weight gain.

Genetic Modification of Differentiated Cells

The islet precursor cells of this invention have a substantial proliferation capacity. If desired, the replication capacity can be further enhanced by increasing the level of telomerase reverse transcriptase (TERT) in the cell, either by increasing transcription from the endogenous gene, or by introducing a transgene. Particularly suitable is the catalytic component of human telomerase (hTERT), provided in International Patent Application WO 98/14592. Transfection and expression of telomerase in human cells is described in Bodnar et al., Science 279:349, 1998 and Jiang et al., Nat. Genet. 21:111, 1999. Genetically altered cells can be assessed for hTERT expression by RT-PCR, telomerase activity (TRAP assay), immunocytochemical staining for hTERT, or replicative capacity, according to standard methods. Other methods of immortalizing cells are also contemplated, such as transforming the cells with DNA encoding myc, the SV40 large T antigen, or MOT-2 (U.S. Pat. No. 5,869,243, International Patent Applications WO 97/32972 and WO 01/23555).

If desired, the cells of this invention can be prepared or further treated to remove undifferentiated cells in vitro, or to safeguard against revertants in vivo. One way of depleting undifferentiated stem cells from the population is to transfect the population with a vector in which an effector gene under control of a promoter that causes preferential expression in undifferentiated cells—such as the TERT promoter or the OCT-4 promoter. The effector gene may be a reporter to guide cell sorting, such as green fluorescent protein. The effector may be directly lytic to the cell, encoding, for example, a toxin, or a mediator of apoptosis, such as caspase (Shinoura et al., Cancer Gene Ther. 7:739, 2000). The effector gene may have the effect of rendering the cell susceptible to toxic effects of an external agent, such as an antibody or a prodrug. Exemplary is a herpes simplex thymidine kinase (tk) gene, which causes cells in which it is expressed to be susceptible to ganciclovir (U.S. Ser. No. 60/253,443). Alternatively, the effector can cause cell surface expression of a foreign determinant that makes any cells that revert to an undifferentiated phenotype susceptible to naturally occurring antibody in vivo (U.S. Ser. No. 60/253,357).

Use of Islet Cells in Research and Clinical Therapy

This invention provides a method to produce large numbers of islet precursor cells, and mature islet cells. These cell populations can be used for a variety of important research, development, and commercial purposes.

The cells of this invention can be used to prepare a cDNA library relatively uncontaminated with cDNA preferentially expressed in cells from other lineages. The differentiated cells of this invention can also be used to prepare monoclonal or polyclonal antibodies that are specific for markers of islet precursors and their derivatives, according to standard methods.

Of particular interest are use of the compositions of this invention for drug development and clinical therapy.

Drug Screening

Islet cells of this invention can be used to screen for factors (such as solvents, small molecule drugs, peptides, polynucleotides) or environmental conditions (such as culture conditions or manipulation) that affect the characteristics of islet precursor cells and their various progeny.

A prime example is the use of islet cell clusters or homogeneous beta cell preparations for the effect of small molecule drugs that have the potential to up- or down-regulate insulin synthesis or secretion. The cells are combined with the test compound, and then monitored for change in expression or secretion rate, for example by RT-PCR or immunoassay of the culture medium.

Other screening methods of this invention relate to the testing of pharmaceutical compounds for a potential effect on islet cell growth, development, or toxicity. This type of screening is appropriate not only when the compound is designed to have a pharmacological effect on islet cells, but also to test for islet-related side-effects of compounds designed for a primary pharmacological effect elsewhere.

In a third example, pPS cells (undifferentiated or differentiated) are used to screen factors that promote maturation into islet cells, or promote proliferation and maintenance of islet cells in long-term culture. For example, candidate differentiation factors or maturation factors are tested by adding them to cells in different wells, and then determining any phenotypic change that results, according to desirable criteria for further culture and use of the cells. This can lead to improved derivation and culture methods for not only pPS derived islets, but also for islet cells and their progenitors isolated from pancreas.

The reader is referred generally to the standard textbook "In vitro Methods in Pharmaceutical Research", Academic Press, 1997, and U.S. Pat. No. 5,030,015. Assessment of the activity of candidate pharmaceutical compounds generally involves combining the differentiated cells of this invention with the candidate compound, either alone or in combination with other drugs. The investigator determines any change in the morphology, marker phenotype, or functional activity of the cells that is attributable to the compound (compared with untreated cells or cells treated with an inert compound), and then correlates the effect of the compound with the observed change.

Cytotoxicity can be determined in the first instance by the effect on cell viability, survival, morphology, and the expression of certain markers and receptors. Effects of a drug on chromosomal DNA can be determined by measuring DNA synthesis or repair. [$^3$H]-thymidine or BrdU incorporation, especially at unscheduled times in the cell cycle, or above the level required for cell replication, is consistent with a drug effect. Unwanted effects can also include unusual rates of sister chromatid exchange, determined by metaphase spread. The reader is referred to A. Vickers (pp 375–410 in "In vitro Methods in Pharmaceutical Research," Academic Press, 1997) for further elaboration.

Reconstitution of Islet Function

This invention also provides for the use of islet precursor cells or their derivatives to restore islet function in a patient in need of such therapy. Any condition relating to inadequate production of a pancreatic endocrine (insulin, glucagon, or somatostatin), or the inability to properly regulate secretion may be considered for treatment with cells prepared according to this invention, as appropriate. Of especial interest is the treatment of Type I (insulin-dependent) diabetes mellitus.

Patients are chosen for treatment based on confirmed long-term dependence on administration of exogenous insulin, and acceptable risk profile. The patient receives approximately 10,000 islet equivalents per kg body weight. To overcome an allotype mismatch, the patient is started before surgery with anti-rejection drugs such as FK506 and rapamycin (orally) and daclizumab (intravenously). The islet cells are infused through a catheter in the portal vein. The patient is then subjected to abdominal ultrasound and blood tests to determine liver function. Daily insulin requirement is tracked, and the patient is given a second transplant if required. Follow-up monitoring includes frequent blood tests for drug levels, immune function, general health status, and whether the patient remains insulin independent.

General approaches to the management of the diabetic patient are provided in standard textbooks, such as the *Textbook of Internal Medicine, 3$^{rd}$ Edition*, by W. N. Kelley ed., Lippincoft-Raven, 1997; and in specialized references such as *Diabetes Mellitus: A Fundamental and Clinical Text 2nd Edition*, by D. Leroith ed., Lippincoft Williams & Wilkins 2000; *Diabetes (Atlas of Clinical Endocrinology Vol. 2)* by C. R. Kahn et al. eds., Blackwell Science 1999; and *Medical Management of Type 1 Diabetes 3$^{rd}$ Edition*, McGraw Hill 1998. Use of islet cells for the treatment of Type I diabetes is discussed at length in *Cellular Inter-*

Relationships in the Pancreas: Implications for Islet Transplantation, by L. Rosenberg et al., Chapman & Hall 1999; and Fetal Islet Transplantation, by C. M. Peterson et al. eds., Kluwer 1995.

As always, the ultimate responsibility for patient selection, the mode of administration, and dosage of pancreatic endocrine cells is the responsibility of the managing clinician.

For purposes of commercial distribution, islet cells of this invention are typically supplied in the form of a pharmaceutical composition, comprising an isotonic excipient prepared under sufficiently sterile conditions for human administration. This invention also includes sets of cells that exist at any time during their manufacture, distribution, or use. The cell sets comprise any combination of two or more cell populations described in this disclosure, exemplified but not limited to a type of differentiated pPS-derived cell (islet cells, their precursors, subtypes, and so on), in combination with undifferentiated pPS cells or other differentiated cell types, sometimes sharing the same genome. Each cell type in the set may be packaged together, or in separate containers in the same facility, or at different locations, under control of the same entity or different entities sharing a business relationship.

For general principles in medicinal formulation of cell compositions, the reader is referred to Cell Therapy: Stem Cell Transplantation, Gene Therapy, and Cellular Immunotherapy, by G. Morstyn & W. Sheridan eds, Cambridge University Press, 1996. The composition is optionally packaged in a suitable container with written instructions for a desired purpose, such as the treatment of diabetes.

Devices

The cells of this invention can also be used as the functional component in a mechanical device designed to produce one or more of the endocrine polypeptides of pancreatic islet cells.

In its simplest form, the device contains the pPS derived islet cells behind a semipermeable membrane that prevents passage of the cell population, retaining them in the device, but permits passage of insulin, glucagon, or somatostatin secreted by the cell population. This includes islet cells that are microencapsulated, typically in the form of cell clusters to permit the cell interaction that inhibits dedifferentiation. For example, U.S. Pat. No. 4,391,909 describe islet cells encapsulated in a spheroid semipermeable membrane made up of polysaccharide polymers >3,000 mol. wt. that are cross-linked so that it is permeable to proteins the size of insulin, but impermeable to molecules over 100,000 mol. wt. U.S. Pat. No. 6,023,009 describes islet cells encapsulated in a semipermeable membrane made of agarose and agaropectin. Microcapsules of this nature are adapted for administration into the body cavity of a diabetic patient, and are thought to have certain advantages in reducing histocompatibility problems or susceptibility to bacteria.

More elaborate devices are also contemplated, either for implantation into diabetic patients, or for extracorporeal therapy. U.S. Pat. No. 4,378,016 describes an artificial endocrine gland containing an extracorporeal segment, a subcutaneous segment, and a replaceable envelope containing the hormone-producing cells. U.S. Pat. No. 5,674,289 describes a bioartificial pancreas having an islet chamber, separated by a semipermeable membrane to one or more vascularizing chambers open to surrounding tissue. Useful devices typically have a chamber adapted to contain the islet cells, and a chamber separated from the islet cells by a semipermeable membrane which collects the secreted proteins from the islet cells, and which may also permit signaling back to the islet cells, for example, of the circulating glucose level.

The following examples are provided as further non-limiting illustrations of particular embodiments of the invention.

EXAMPLES

Example 1

Feeder-free Propagation of Embryonic Stem Cells

Established lines of undifferentiated human embryonic stem (hES) cells were maintained in a culture environment essentially free of feeder cells.

Conditioned medium prepared in advance using primary mouse embryonic fibroblasts (mEF) isolated according to standard procedures (WO 01/51616). Fibroblasts were harvested from T150 flasks by washing once with $Ca^{++}/Mg^{++}$ free PBS and incubating in 1.5–2 mL trypsin/EDTA (Gibco) for ~5 min. After fibroblasts detached from the flask, they were collected in mEF medium (DMEM+10% FBS). The cells were irradiated at 4000 rad, counted, and seeded at ~55,000 cells $cm^{-2}$ in mEF medium. After at least 4 h, the medium were exchanged with SR containing ES medium (80% knockout DMEM (Gibco BRL, Rockville Md.), 20% knockout serum replacement (Gibco), 1% non-essential amino acids (Gibco), 1 mM L-glutamine (Gibco), 0.1 mM β-mercaptoethanol (Sigma, St. Louis, Mo.), supplemented with 4 ng/mL recombinant human basic fibroblast growth factor (bFGF; Gibco). About 0.3–0.4 mL of medium was conditioned per $cm^2$ of plate surface area. Before addition to the hES cultures, the conditioned medium was supplemented with another 4 ng/mL of human bFGF.

Plates for culturing the hES cells were coated with Matrigel® (Becton-Dickinson, Bedford Mass.) by diluting stock solution ~1:30 in cold KO DMEM, dispensing at 0.75–1.0 mL per 9.6 $cm^2$ well, and incubating for 4 h at room temp or overnight at 4° C.

hES cultures were passaged by incubation in ~200 U/mL collagenase IV for ~5–10 min at 37° C. Cells were harvested by removing individual colonies up with a Pipetman™ under a microscope or scraping, followed by gentle dissociation into small clusters in conditioned medium, and then seeded onto Matrigel® coated plates. About one week after seeding, the cultures became confluent and could be passaged. Cultures maintained under these conditions for over 180 days continued to display ES-like morphology. SSEA-4, Tra-1-60, Tra-1-81, and alkaline phosphatase were expressed by the hES colonies, as assessed by immunocytochemistry, but not by the differentiated cells in between the colonies.

Expression of the undifferentiated hES cell markers was assayed by reverse-transcriptase PCR amplification. The transcription factor Oct-4 is normally expressed in the undifferentiated hES cells and is down-regulated upon differentiation. Cells maintained on Matrigel® in conditioned medium for 21 days expressed hTERT and Oct-4. Telomerase activity was measured by TRAP assay (Kim et al., Science 266:2011, 1997; Weinrich et al., Nature Genetics 17:498, 1997). Cells maintained in the feeder-free culture were telomerase positive.

Pluripotency of undifferentiated cells cultured without feeders was determined by differentiating the cells through the formation of embryoid bodies. Confluent monolayer cultures of hES cells were harvested by incubating in 1 mg/mL collagenase for 5–20 min, and dissociated into clusters. They were then plated in non-adherent cell culture plates (Costar) in a medium composed of 80% KO DMEM (Gibco) and 20% non-heat-inactivated FBS (Hyclone), supplemented with 1% non-essential amino acids, 1 mM glutamine, 0.1 mM β-mercaptoethanol. The embryoid bodies were fed every other day by the addition of 2 mL of medium per well. After 4–8 days in suspension, they were then cultured on poly-ornithine coated plates for about 7 days.

Immunocytochemistry showed staining patterns consistent with cells of the neuron and cardiomyocyte lineages, and cells staining for α-fetoprotein, a marker of endoderm lineage. The undifferentiated cells were also tested for their ability to form teratomas by intramuscular injection into SCID mice. Resulting tumors were excised after 78–84 days. Cell types from all three germ layers were identified by histological analysis.

Example 2

Derivation of Hepatocytes from hES Cells

Undifferentiated hES cells were differentiated into cells having characteristics of human hepatocytes using a strategy to initiate a global differentiation process using DMSO in a subconfluent culture. The cells are then induced to form hepatocyte-like cells by the addition of Na-butyrate.

Briefly, the hES cells were maintained in undifferentiated culture conditions for 2–3 days after splitting. At this time, the cells were 50 to 60% confluent and the medium was exchanged with unconditioned SR medium containing 1% DMSO (Step II). The cultures were fed daily with SR medium for 4 days and then exchanged into unconditioned SR medium containing both 1% DMSO and 2.5% Na-butyrate, with which they were fed daily for 6 days (Step III). They were then replated onto collagen, and cultured in a hepatocyte maturation medium containing a cocktail of hepatocyte-friendly growth factors (Step IV). The procedure is summarized in Table 3.

TABLE 3

Hepatocyte Differentiation Protocol

| Step I<br>Undifferentiated<br>cells<br>(until confluent) | Step II<br>Pre-<br>differentiation<br>(4 days) | Step III<br>Hepatocyte<br>differentiation<br>(6 days) | Step IV<br>Hepatocyte<br>maturation (Groups<br>7–9 only; 4 days) |
|---|---|---|---|
| Feeder-free<br>conditions | 20% SR<br>medium +<br>1% DMSO | 20% SR<br>medium +<br>1% DMSO +<br>2.5 mM<br>butyrate | HCM +<br>30 ng/mL hEGF +<br>10 ng/mL TGF-α +<br>30 ng/mL HGF +<br>2.5 mM butyrate |

FIG. 1 shows the hepatocyte-like cells that were obtained. Left column: 10× magnification; Right column: 40× magnification. By 4 days in the presence of butyrate, more than 80% of cells in the culture are large in diameter, containing large nuclei and granular cytoplasm (Row A). After 5 days in SR medium, the cells were switched to HCM. Two days later, many cells are multinucleated, and have a large polygonal shape (Row B). By 4 days in HCM, multinucleated polygonal cells are common, and have a darker cytosol (Row C), by which criteria they resemble freshly isolated human adult hepatocytes (Row D) or fetal hepatocytes (Row E).

Example 3

Obtaining Insulin-secreting Cells from Early Cells in the Hepatocyte Pathway

Insulin-secreting cells were derived from hES cells of the H9 line using a modification of the hepatocyte differentiation protocol described in the last Example.

Briefly, in Step I, hES cells were grown to confluence after their last passage over a 7–8 day period using SR medium conditioned by mouse embryonic fibroblasts as described in Example 1. In Step II, the medium was exchanged with unconditioned SR medium containing 1% DMSO, to which 10 μM cyclopamine was added, and the cells were cultured for 4 days. In Step III, the cells were cultured for 11 days in RPMI1640 medium with B27 supplement, containing 0.5 mM butyrate (5-fold lower than the hepatocyte protocol), 10 μM cyclopamine, 4 nM activin A and 10 mM nicotinamide. The cells were then harvested, fixed, and stained for insulin expression (using the Sigma mouse monoclonal anti-insulin antibody at a dilution of 1:500) and counterstained with DAPI to detect nuclei. In Step IV, the cells are matured RPMI1640/B27 by culturing for 11 days in RPMI supplemented with B27, and containing possible islet differentiation factors.

FIG. 2 shows the results in which the cells were cultured in Step IV with 4 nM activin A, 4 nM betacellulin, 10 nM IGF-1, and 10 mM nicotinamide. The round circles in the upper panel represent the DAPI blue-stained nuclei. The diffuse staining centered in the middle of the field is red fluorescent staining, representing insulin synthesized and fixed within the cell. It was estimated that about 1% of the cells in the well were expressing insulin. No insulin staining was observed in other cell clusters on the same slide or in the isotype control.

Example 4

Entering the Islet Cell Pathway by Optimizing Formation of Gut Endoderm

This example provides an illustration of the stepwise induction of islets from pPS cells, mimicking the normal development that occurs in utero.

The H7 and H9 line of hES cells were grown to confluence using standard feeder free conditions, which served as starting material for the experiment. To initiate differentiation, the medium was changed to RPMI 1640 supplemented with B27 (Invitrogen) and one of the following alternatives:

no further additives (medium control)

4 nM Activin A (R&D systems)

0.5 mM sodium butyrate (Sigma)

both Activin A and butyrate together.

The medium was exchanged daily (with the exception of one day) for a total of 8 treatment days.

At the end of this period, the medium was removed, the cells were rinsed with PBS, and a cell lysate was prepared by the addition of 400 μL of RTL lysis buffer (Qiagen). RNA was prepared using the Qiagen RNAeasy Mini kit according to the manufacturer's instructions. The RNA was treated with DNAse, and random primed first strand cDNA was prepared using the Invitrogen Preamplification First Strand cDNA kit following manufacturer's instructions. Standard real-time RT-PCR (Taqman) was carried out on each cDNA sample using primer and probe sets for Sox17, HNF1 alpha, and HNF3beta. To normalize expression levels, parallel Taqman assay was run using the probe and primer set for cycophilin (Applied Biosystems). The relative abundance of each sample compared to a pancreas standard was calculated using the delta delta Ct method (Applied Biosystems).

FIG. 3 shows expression levels of the markers for gut endoderm. Results are standardized to the expression level in human fetal pancreas. Also shown for comparison is the level of expression in undifferentiated hES cells (the starting cell line). The three markers were induced most effectively by the combination of both Activin A and sodium butyrate. Sox17 was expressed at high levels (2.3 relative expression) in undifferentiated H9 cells, but was induced to 32 relative expression level with the two additives (more than 100-fold increase). In H7 cells, the level of induction was more dramatic, going from 0.007 times fetal pancreas to 79 times fetal pancreas (more than 10,000-fold increase). HNF3beta increased from less than 0.5 relative expression to 5.1 or 6.3 (more than 10-fold increase). The levels of HNF4alpha increased from less than 0.1 relative expression level to over 1.0 (more than 10-fold increase).

The robust induction of these three markers confirms that these hES derived cells have key characteristics of gut endoderm. These cells are next subcultured and treated with factors that induce pancreas formation, monitored by induction of the key pancreas marker Pdx1.

Example 5

Obtaining Islet Cells by Using Additives in Long-term Aggregate Culture

The H7 line of hES cells was grown in an undifferentiated form in mEF medium as in Example 1. They were then grown in suspension culture (forming embryoid bodies) in a blended medium consisting of mEF conditioned medium and DFB+ at 1:1. DFB+ is DMEM/F12 medium supplemented with B27 additive (1×), insulin (25 µg/ml), progesterone (6.3 ng/ml), putrescine (10 µg/ml), selenium (in the form of selenite, 100 ng/ml), transferrin (50 µg/ml), and the thyroid hormone receptor ligand T3 (40 ng/ml). The next day, 10 µM all-trans retinoic acid was added. On the third day, the medium was changed to DFB+ with 10 µM all trans retinoic acid, then fed every other day for 7 days (Stage 1).

To initiate Stage 2, all-trans retinoic acid was removed and replaced with medium containing Noggin (200 ng/ml), EGF (20 ng/ml) and bFGF (2 ng/ml). The cells were fed every other day for 14 days.

For Stage 3, Noggin, EGF and bFGF were withdrawn, and the cells were cultured in DFB+ containing nicotinamide (10 mM). The medium was changed every other day for 5 days. The cells were then plated on coated chamber slides for one day, fixed and stained with antibodies against the c-peptide of insulin, or somatostatin. c-Peptide is a component of proinsulin that is removed before secretion. It is useful in distinguishing insulin synthesized from the cell from insulin present as a component of the medium.

FIG. 4 shows the results. The top and middle panels show staining for insulin c-peptide at low and high magnification, indicating a cluster of mature pancreatic beta cells. The bottom panel shows staining for somatostatin, a marker of islet delta cells. Taqman real-time RT-PCR confirmed that insulin and glucagon are expressed by these cells at the mRNA level.

Example 6

Driving the End-stage Islet Pathway by Neurogenin 3 Gene Expression

This experiment demonstrates the effectiveness of over-expressing an islet related gene in recruiting a gene expression profile characteristic of the islet cell lineage during Stage III of differentiation.

An adenovirus vector was constructed containing the transcription regulator gene Neurogenin 3 (Ngn3) under control of a constitutive promoter. AdNgn3 is a replication deficient, E1- and E3-deleted recombinant adenovirus 5 based vector constructed using the AdMAX™ vector construction kit (Microbix Biosystems, Toronto). Ngn3 cDNA 645 bp (GenBank accession # NM_020999) was cloned into pDC515 shuttle vector downstream of mCMV (Murine Cytomegalovirus Immediate Early Gene) promoter. A natural sequence TAGAAAGG immediately upstream of ATG start codon was replaced with the consensus Kozak sequence GCCACC. The shuttle plasmid containing the Ngn3 insert and the Ad genomic plasmid (AdMAX plasmid) were cotransfected into E1-expressing 293 cells for homologous recombination to occur. Plaques were isolated, the viral stock was amplified in 293 cells, and then purified by CsCI density gradient centrifugation. Viral particle concentration was determined by measuring optical density at $A_{260}$, and the infectious titer was determined by standard plaque assay.

Human ES cells of the H7 line were suspended and cultured in blended medium as in Example 5. All-trans retinoid acid (10 µM) was added to the medium the next day. Seven days later, the EBs were plated on Matrigel® in DFB+ medium plus EGF (20 ng/ml) and bFGF (2 ng/ml). After five days in culture, cells were infected with the AdNgn3 vector at MOI of 50. AdGFP (an equivalent vector containing the gene for green fluorescent protein, not expected to direct differentiation) was used as a negative control. AdNgn3 or AdGFP virus at an MOI of 50 was applied directly to cells in 6-well plates in 1 mL of DFB+ medium containing EGF (20 ng/ml) for 4 h, then additional 2 mL of the same medium was added to each well. The medium was replenished every other day thereafter. Cells were harvested 2 days or 8 days after the infection, and RNA was isolated for analysis by real-time RT-PCR as in Example 4. Cells plated on chamber slides for immunohistochemistry were fixed in 4% paraformaldehyde, blocked, and stained with antibody against glucagon (1:1000), followed by FITC conjugated goat anti-mouse IgG (1:500).

FIG. 5 shows immunocytochemical staining of the Neurogenin 3 transduced cells 9 days after transduction. This plated embryoid body shows a substantial level of antibody-detectable glucagon expression.

FIGS. 6(A) and (B) shows mRNA expression levels in the Neurogenin 3 transduced cells (solid bars), compared with the negative control (hatched bars). Real-time RT-PCR data is normalized to expression levels in human fetal pancreas.

It was found that several genes that are downstream of Neurogenin 3 were specifically up-regulated in the transduced cells, compared with controls. NeuroD1 and Nkx2.2 were both substantially upregulated by day 2; Nkx6.1 was upregulated by day 8. Insulin and glucagon expression were also substantially up-regulated by day 8, indicating that the gene transfection strategy substantially improves maturation to cells making the clinically important end-stage products of islet cells.

The skilled reader will appreciate that the invention can be modified as a matter of routine optimization, without departing from the spirit of the invention, or the scope of the appended claims.

What is claimed as the invention is:

1. A method for obtaining human insulin secreting cells, comprising
   a) culturing hES cells in a first medium comprising Activin A; and
   b) maturing the cells from a) in a second medium comprising nicotinamide; thereby obtaining a population comprising human insulin secreting cells.

2. The method of claim 1, wherein the first medium further comprises n-butyrate.

3. A method for obtaining human insulin secreting cells, comprising
   a) culturing hES cells in a suspension culture to form embryoid bodies;
   b) culturing the cells from a) in a medium comprising trans-retinoic acid;
   c) culturing the cells from b) in a medium comprising a TGF-β antagonist and one or more mitogens; and
   d) maturing the cells from c) in a medium comprising nicotinamide; thereby obtaining a population comprising human insulin-secreting cells.

4. The method of claim 3, wherein the TGF-β antagonist is Noggin.

5. The method of claim 3, wherein the mitogen(s) is selected from the group consisting of EGF, bFGF, and betacellulin.

6. A method for obtaining human insulin secreting cells, comprising:

a) culturing hES cells in a first medium comprising Activin A;
b) culturing the cells from step a) in a second medium comprising a TGF-β antagonist and one or more mitogens; and
c) culturing the cells from step b) in a third medium comprising nicotinamide; thereby obtaining a population comprising human insulin-secreting cells.

7. The method of claim 6, wherein the TGF-β antagonist is Noggin.

8. The method of claim 6, wherein the mitogen(s) is selected from the group consisting of epidermal growth factor (EGF), basic fibroblast growth factor (bFGF), and betacellulin.

9. The method of claim 6, wherein the second medium comprises Noggin, EGF, and bFGF.

10. The method of claim 6, wherein the second medium comprises Noggin, betacellulin, and bFGF.

* * * * *

SEQUENCE LISTING

<160> NUMBER OF SEQ ID NOS: 45

<210> SEQ ID NO 1
<211> LENGTH: 21
<212> TYPE: DNA
<213> ORGANISM: Homo sapiens

<400> SEQUENCE: 1
cagcctttgt gaaccaacac c                                          21

<210> SEQ ID NO 2
<211> LENGTH: 20
<212> TYPE: DNA
<213> ORGANISM: Homo sapiens

<400> SEQUENCE: 2
cgttccccgc acactaggta                                            20

<210> SEQ ID NO 3
<211> LENGTH: 23
<212> TYPE: DNA
<213> ORGANISM: Homo sapiens

<400> SEQUENCE: 3
cggctcacac ctggtggaag ctc                                        23

<210> SEQ ID NO 4
<211> LENGTH: 16
<212> TYPE: DNA
<213> ORGANISM: Homo sapiens

<400> SEQUENCE: 4
ctggagggac gcacgc                                                16

<210> SEQ ID NO 5
<211> LENGTH: 21
<212> TYPE: DNA
<213> ORGANISM: Homo sapiens

<400> SEQUENCE: 5
tcccgtcttt gtccaacaaa a                                          21

<210> SEQ ID NO 6
<211> LENGTH: 26
<212> TYPE: DNA
<213> ORGANISM: Homo sapiens

<400> SEQUENCE: 6
tggcctgtac ccctcatcaa ggatcc                                     26

<210> SEQ ID NO 7
<211> LENGTH: 18
<212> TYPE: DNA
<213> ORGANISM: Homo sapiens

<400> SEQUENCE: 7
tggcgttgtt tgtggctg                                              18

<210> SEQ ID NO 8
<211> LENGTH: 19
<212> TYPE: DNA
<213> ORGANISM: Homo sapiens

-continued

```
<400> SEQUENCE: 8
aggtcccaag gtggagtgc                                            19

<210> SEQ ID NO 9
<211> LENGTH: 23
<212> TYPE: DNA
<213> ORGANISM: Homo sapiens

<400> SEQUENCE: 9
tgcgcacatc cctgccctcc tac                                       23

<210> SEQ ID NO 10
<211> LENGTH: 20
<212> TYPE: DNA
<213> ORGANISM: Homo sapiens

<400> SEQUENCE: 10
tctctattct tttgcgccgg                                           20

<210> SEQ ID NO 11
<211> LENGTH: 18
<212> TYPE: DNA
<213> ORGANISM: Homo sapiens

<400> SEQUENCE: 11
cttggacagt gggcgcac                                             18

<210> SEQ ID NO 12
<211> LENGTH: 25
<212> TYPE: DNA
<213> ORGANISM: Homo sapiens

<400> SEQUENCE: 12
agaaaggatg acgcctcaac cctcg                                     25

<210> SEQ ID NO 13
<211> LENGTH: 20
<212> TYPE: DNA
<213> ORGANISM: Homo sapiens

<400> SEQUENCE: 13
aaggcaggag aatcgcttga                                           20

<210> SEQ ID NO 14
<211> LENGTH: 18
<212> TYPE: DNA
<213> ORGANISM: Homo sapiens

<400> SEQUENCE: 14
tggtgcaatc tcggctca                                             18

<210> SEQ ID NO 15
<211> LENGTH: 20
<212> TYPE: DNA
<213> ORGANISM: Homo sapiens

<400> SEQUENCE: 15
cccaggaggc ggaggttgca                                           20

<210> SEQ ID NO 16
<211> LENGTH: 21
<212> TYPE: DNA
```

<213> ORGANISM: Homo sapiens

<400> SEQUENCE: 16
ccgactggag cagctactat g                                      21

<210> SEQ ID NO 17
<211> LENGTH: 20
<212> TYPE: DNA
<213> ORGANISM: Homo sapiens

<400> SEQUENCE: 17
tacgtgttca tgccgttcat                                        20

<210> SEQ ID NO 18
<211> LENGTH: 23
<212> TYPE: DNA
<213> ORGANISM: Homo sapiens

<400> SEQUENCE: 18
cagagcccga gggctactcc tcc                                    23

<210> SEQ ID NO 19
<211> LENGTH: 18
<212> TYPE: DNA
<213> ORGANISM: Homo sapiens

<400> SEQUENCE: 19
caggcccaga aggtcatc                                          18

<210> SEQ ID NO 20
<211> LENGTH: 18
<212> TYPE: DNA
<213> ORGANISM: Homo sapiens

<400> SEQUENCE: 20
gggagggagg ccataatc                                          18

<210> SEQ ID NO 21
<211> LENGTH: 19
<212> TYPE: DNA
<213> ORGANISM: Homo sapiens

<400> SEQUENCE: 21
atctgccatc ggggcaccc                                         19

<210> SEQ ID NO 22
<211> LENGTH: 20
<212> TYPE: DNA
<213> ORGANISM: Homo sapiens

<400> SEQUENCE: 22
aataccaaag aggtggcgca                                        20

<210> SEQ ID NO 23
<211> LENGTH: 19
<212> TYPE: DNA
<213> ORGANISM: Homo sapiens

<400> SEQUENCE: 23
atggcctgtg ggatgctgt                                         19

<210> SEQ ID NO 24
<211> LENGTH: 24

```
<212> TYPE: DNA
<213> ORGANISM: Homo sapiens

<400> SEQUENCE: 24
cgtatcacca ccgagctcaa gcgc                                           24

<210> SEQ ID NO 25
<211> LENGTH: 20
<212> TYPE: DNA
<213> ORGANISM: Homo sapiens

<400> SEQUENCE: 25
gctgccaagg aattcattgc                                                20

<210> SEQ ID NO 26
<211> LENGTH: 22
<212> TYPE: DNA
<213> ORGANISM: Homo sapiens

<400> SEQUENCE: 26
cttcaacaat ggcgacctct tc                                             22

<210> SEQ ID NO 27
<211> LENGTH: 24
<212> TYPE: DNA
<213> ORGANISM: Homo sapiens

<400> SEQUENCE: 27
tgaaaggccg aggaaggcga gatt                                           24

<210> SEQ ID NO 28
<211> LENGTH: 20
<212> TYPE: DNA
<213> ORGANISM: Homo sapiens

<400> SEQUENCE: 28
gctggggtga cctcaatcta                                                20

<210> SEQ ID NO 29
<211> LENGTH: 20
<212> TYPE: DNA
<213> ORGANISM: Homo sapiens

<400> SEQUENCE: 29
caggaacctg catgaggact                                                20

<210> SEQ ID NO 30
<211> LENGTH: 23
<212> TYPE: DNA
<213> ORGANISM: Homo sapiens

<400> SEQUENCE: 30
agtttcagag ccattgggcg gtg                                            23

<210> SEQ ID NO 31
<211> LENGTH: 23
<212> TYPE: DNA
<213> ORGANISM: Homo sapiens

<400> SEQUENCE: 31
tcactgctca ggacctacta aca                                            23

<210> SEQ ID NO 32
```

```
<211> LENGTH: 18
<212> TYPE: DNA
<213> ORGANISM: Homo sapiens

<400> SEQUENCE: 32
gaggaccttg gggctgag                                                  18

<210> SEQ ID NO 33
<211> LENGTH: 23
<212> TYPE: DNA
<213> ORGANISM: Homo sapiens

<400> SEQUENCE: 33
tacagcgaga gtgggctgat ggg                                            23

<210> SEQ ID NO 34
<211> LENGTH: 21
<212> TYPE: DNA
<213> ORGANISM: Homo sapiens

<400> SEQUENCE: 34
gagatccatg gtgttcaagg a                                              21

<210> SEQ ID NO 35
<211> LENGTH: 20
<212> TYPE: DNA
<213> ORGANISM: Homo sapiens

<400> SEQUENCE: 35
gtcaaggatg cgtatggaca                                                20

<210> SEQ ID NO 36
<211> LENGTH: 23
<212> TYPE: DNA
<213> ORGANISM: Homo sapiens

<400> SEQUENCE: 36
ctacattgtc cctcggcact gcc                                            23

<210> SEQ ID NO 37
<211> LENGTH: 20
<212> TYPE: DNA
<213> ORGANISM: Homo sapiens

<400> SEQUENCE: 37
cagcagaatc cagacctgca                                                20

<210> SEQ ID NO 38
<211> LENGTH: 19
<212> TYPE: DNA
<213> ORGANISM: Homo sapiens

<400> SEQUENCE: 38
gtcagcgcct tccacgact                                                 19

<210> SEQ ID NO 39
<211> LENGTH: 24
<212> TYPE: DNA
<213> ORGANISM: Homo sapiens

<400> SEQUENCE: 39
acgccgagtt gagcaagatg ctgg                                           24
```

-continued

```
<210> SEQ ID NO 40
<211> LENGTH: 18
<212> TYPE: DNA
<213> ORGANISM: Homo sapiens

<400> SEQUENCE: 40
gccacctcgc tcatgctc                                              18

<210> SEQ ID NO 41
<211> LENGTH: 19
<212> TYPE: DNA
<213> ORGANISM: Homo sapiens

<400> SEQUENCE: 41
ccatttcatc cgccggttc                                             19

<210> SEQ ID NO 42
<211> LENGTH: 26
<212> TYPE: DNA
<213> ORGANISM: Homo sapiens

<400> SEQUENCE: 42
ccgagaccca gggaagattt ggttcc                                     26

<210> SEQ ID NO 43
<211> LENGTH: 19
<212> TYPE: DNA
<213> ORGANISM: Homo sapiens

<400> SEQUENCE: 43
cgagggcctt cagtactcc                                             19

<210> SEQ ID NO 44
<211> LENGTH: 20
<212> TYPE: DNA
<213> ORGANISM: Homo sapiens

<400> SEQUENCE: 44
ttgtcattgt ccggtgactc                                            20

<210> SEQ ID NO 45
<211> LENGTH: 23
<212> TYPE: DNA
<213> ORGANISM: Homo sapiens

<400> SEQUENCE: 45
actcaagctc caagtccccg gag                                        23
```